(12) United States Patent
Suzumura et al.

(10) Patent No.: US 8,716,230 B2
(45) Date of Patent: May 6, 2014

(54) METHODS FOR TREATMENT OR PREVENTION OF DISEASES ASSOCIATED WITH FUNCTIONAL DISORDER OF REGULATORY T CELLS

(75) Inventors: Akio Suzumura, Aichi (JP); Jinyan Wang, Aichi (JP); Takashi Matsui, Kanagawa (JP); Sadatoshi Sakuma, Kanagawa (JP); Shin Miyakawa, Tokyo (JP); Masatoshi Fujiwara, Tokyo (JP); Yoshikazu Nakamura, Tokyo (JP)

(73) Assignee: Ribomic Inc., Tokyo (JP)

( * ) Notice: Subject to any disclaimer, the term of this patent is extended or adjusted under 35 U.S.C. 154(b) by 0 days.

(21) Appl. No.: 12/902,389

(22) Filed: Oct. 12, 2010

(65) Prior Publication Data

US 2011/0086906 A1   Apr. 14, 2011

Related U.S. Application Data

(62) Division of application No. 12/084,907, filed as application No. PCT/JP2006/322659 on Nov. 14, 2006.

(30) Foreign Application Priority Data

Nov. 14, 2005 (JP) ................................. 2005-329418

(51) Int. Cl.
*A61K 51/08* (2006.01)
*A61K 31/7088* (2006.01)
*C07K 2/00* (2006.01)
*C07H 21/04* (2006.01)

(52) U.S. Cl.
USPC ........................ 514/17.9; 514/44 R; 536/23.1

(58) Field of Classification Search
None
See application file for complete search history.

(56) References Cited

U.S. PATENT DOCUMENTS

| | | | | |
|---|---|---|---|---|
| 6,083,907 | A * | 7/2000 | Uchida et al. .................. | 514/9.7 |
| 6,329,145 | B1 * | 12/2001 | Janjic et al. ........................ | 435/6 |
| 2003/0072739 | A1 * | 4/2003 | Takada et al. ................. | 424/85.1 |

FOREIGN PATENT DOCUMENTS

| | | |
|---|---|---|
| EP | 2 096 167 | 9/2009 |
| WO | 99/03493 | 1/1999 |
| WO | 2004/036221 | 4/2004 |
| WO | 2004/085642 | 10/2004 |
| WO | WO 2006/074179 | * 7/2006 |

OTHER PUBLICATIONS

Baranzini SE. Systems-based medicine approaches to understand and treat complex diseases. The example of multiple sclerosis. Autoimmunity. Dec. 2006;39(8):651-62.*

Bowie et al. Deciphering the message in protein sequences: tolerance to amino acid substitutions. Science, (Mar. 16, 1990) 247(4948) 1306-10.*

Ngo et al., in The Protein Folding Problem and Tertiary Structure Prediction, Merz and Le Grand (Eds), Aug. 1994, Springer Verlag, pp. 433 and 492-495.*

Aptamer, from Wikipedia, the free encyclopedia [online], [retrieved on May 17, 2011]. Retrieved from the internet: URL<http://en.wikipedia.org/wiki/Aptamer>.*

Lawson et al. Early rheumatoid arthritis is associated with a deficit in the CD4+CD25high regulatory T cell population in peripheral blood. Rheumatology (Oxford). Oct. 2006;45(10):1210-7. Epub Mar. 29, 2006.*

Crispin et al. Quantification of regulatory T cells in patients with systemic lupus erythematosus. J Autoimmun. Nov. 2003;21(3):273-6.*

International Search Report issued Feb. 27, 2010 in International (PCT) Application No. PCT/JP2006/322659 (in English).

Liu X et al. Basic FGF and FGF receptor 1 are expressed in microglia during experimental autoimmune encephalomyelitis: temporally distinct expression of midkine and pleiotrophin. Glia. Dec. 1998;24(4):390-7.

MIR Preclinical Services 2010, *MIR Preclinical Services: Models of Arthritis and Inflammation.* http://www.molecularimaging.com/inflammation_arthitis.htm>. [Jul. 29, 2010].

Tsutsui, J. et al., *A New Family of Heparin-binding Growth/Differentiation Factors: Increased Midkine Expression in Wilms' Tumor and Other Human Carcinomas, Cancer Research*, vol. 53 (Mar. 15, 1993), pp. 1281-1285.

Kadomatsu, K. et al., *Midkine induces the transformation of NIH3T3 cells, British Journal of Cancer*, vol. 75, No. 3 (1997), pp. 354-359.

Horiba, M. et al., *Neointima formation in a restenosis model is suppressed in midkine-deficient mice, The Journal of Clinical Investigation*, vol. 105, No. 4 (Feb. 2000), pp. 489-495.

Sato, W. et al., *Midkine Is Involved in Neutrophil Infiltration into the Tubulointerstitium in Ischemic Renal Injury, The Journal of Immunology*, vol. 167 (2001), pp. 3463-3469.

Takada, T. et al., *Midkine, a Retinoic Acid-Inducible Heparin-Binding Cytokine in Inflammatory Responses: Chemotactic Activity to Neutrophils and Association with Inflammatory Synovitis, J. Biochem*, vol. 122, No. 2 (1997), pp. 453-458.

(Continued)

*Primary Examiner* — David Romeo
(74) *Attorney, Agent, or Firm* — Wenderoth, Lind & Ponack, L.L.P.

(57) ABSTRACT

The inventors examined the role of MK in experimental autoimmune encephalomyelitis, which is a human model for multiple sclerosis. As a result, they discovered that MK has the effect of inhibiting regulatory T cells, and that the autoimmune mechanism induced by type 1 helper T cells can be suppressed by inhibiting MK expression or its activity, thereby increasing the number of regulatory T cells. Furthermore, it was found that diseases associated with the functional disorder of regulatory T cells can be treated with the administration of an inhibitor that inhibits MK expression or activity.

2 Claims, 9 Drawing Sheets

(56) References Cited

OTHER PUBLICATIONS

Maruyama, K. et al., *Midkine, a Heparin-Binding Growth Factor, Is Fundamentally Involved in the Pathogenesis of Rheumatoid Arthritis*, Arthritis & Rheumatism, vol. 50, No. 5 (May 2004), pp. 1420-1429.
Shevach, E., *Regulatory T Cells in Autoimmunity*, Annu. Rev. Immunol, vol. 18 (2000), pp. 423-449.
McGuirk, P. et al., *Pathogen-specific regulatory T cells provoke a shift in the Th1/Th2 paradigm in immunity to infectious diseases*, Trends in Immunology, vol. 23, No. 9 (Sep. 2002), pp. 450-455.
Roncarolo, M. et al., *The role of different subsets of T regulatory cells in controlling autoimmunity*, Current Opinion in Immunology, vol. 12 (2000), pp. 676-683.
Jonuleit, H. et al., *Induction of Interleukin 10-producing, Nonproliferating $CD4^+$ T Cells with Regulatory Properties by Repetitive Stimulation with Allogeneic Immature Human Dendritic Cells*, J. Exp. Med., vol. 192, No. 9 (Nov. 6, 2000), pp. 1213-1222.
Sakaguchi, S., *New perspectives of immune regulation mediated by Tcells*, Exp. Med., vol. 21, No. 16 (2003), pp. 2164-2168 (in the Japanese Language only).
Viglietta, V. et al., *Loss of Functional Suppression by $CD4^+$ $CD25^+$ Regulatory T Cells in Patients with Multiple Sclerosis*, J. Exp. Med., vol. 199, No. 7 (Apr. 5, 2004), pp. 971-979.
Haas, J. et al., *Reduced suppressive effect of $CD4^+$ $CD25^{high}$ regulatory T cells on the T cell immune response against myelin oligodendrocyte glycoprotein in patients with multiple sclerosis*, Eur. J. Immunol., vol. 35 (2005), pp. 3343-3352.
Huan, J. et al., *Decreased FOXP3 Levels in Multiple Sclerosis Patients*, Journal of Neuroscience Research, vol. 81 (2005), pp. 45-52.
Furtado, C. et al., *Regulatory T cells in spontaneous autoimmune encephalomyelitis*, Immunological Reviews, vol. 182 (2001), pp. 122-134.
Hori, S. et al., *Specificity requirements for selection and effector functions of $CD25^+$ $4^+$ regulatory T cells in anti-myelin basic protein T cell receptor transgenic mice*, Proc. Natl. Acad. Sci. USA, vol. 99, No. 12 (Jun. 11, 2002), pp. 8213-8218.
Kohm, A. et al., *Cutting Edge: $CD4^+$ $CD25^+$ Regulatory T Cells Suppress Antigen-Specific Autoreactive Immune Responses and Central Nervous System Inflammation During Active Experimental Autoimmune Encephalomyelitis*, The Journal of Immunology, vol. 169 (2002), pp. 4712-4716.
Balandina, A. et al., *Functional defect of regulatory $CD4^+$ $CD25^+$ T cells in the thymus of patients with autoimmune myasthenia gravis*, Blood, vol. 105, No. 2 (Jan. 15, 2005), pp. 735-741.
Coombes, J. et al., *Regulatory T cells and intestinal homeostasis*, Immunological Reviews, vol. 204 (2005), pp. 184-194.
Read, S. et al., *Cytotoxic T Lymphocyte-associated Antigen 4 Plays an Essential Role in the Function of $CD25^+$ $CD4^+$ Regulatory Cells that Control Intestinal Inflammation*, J. Exp. Med., vol. 192, No. 2 (Jul. 17, 2000), pp. 295-302.
Alvarado-Sanchez, B. et al., *Regulatory T cells in patients with systemic lupus erythematosus*, Journal of Autoimmunity, vol. 27 (2006), pp. 110-118.
Green, E. et al., *$CD4^+$ $CD25^+$ T regulatory cells control anti-islet $CD8^+$ T cells through TGF-β-TGF-β receptor interactions in type 1 diabetes*, Proc. Natl. Acad. Sci. USA, vol. 100, No. 19 (Sep. 16, 2003), pp. 10878-10883.
Dai, Z. et al., *$CD4^+$ $CD25^+$ regulatory T cells suppress allograft rejection mediated by memory $CD8^+$ T cells via a CD30-dependent mechanism*, The Journal of Clinical Investigation, vol. 113, No. 2 (Jan. 2004), pp. 310-317.
Wei, W. et al., *Anti-tumor immunity and autoimmunity: a balancing act of regulatory T cells*, Cancer Immunol Immunother, vol. 53 (2004), pp. 73-78.
Frey, O. et al., *The role of regulatory T cells in antigen-induced arthritis: aggravation of arthritis after depletion and amelioration after transfer of $CD4^+$ $CD25^+$ T cells*, Arthritis Res. Ther., vol. 7, No. 2 (2005), pp. R291-R301.
Lan, R. et al., *Regulatory T cells: Development, function and role in autoimmunity*, Autoimmunity Reviews, vol. 4 (2005), pp. 351-363.
Sakaguchi, S. et al., *Organ-Specific Autoimmune Diseases Induced in Mice by Elimination of T Cell Subset*, J. Exp. Med., vol. 161 (Jan. 1, 1985), pp. 72-87.
Itoh, M. et al., *Thymus and Autoimmunity: Production of $CD25^+$ $CD4^+$ Naturally Anergic and Suppressive T Cells as a Key Function of the Thymus in Maintaining Immunologic Self-Tolerance*, The Journal of Immunology, vol. 162 (1999), pp. 5317-5326.
Jonuleit, H. et al., *Identification and Functional Characterization of Human $CD4^+$ $CD25^+$ T Cells with Regulatory Properties Isolated from Peripheral Blood*, J. Exp. Med., vol. 193, No. 11 (Jun. 4, 2001), pp. 1285-1294.
Levings, M. et al., *Human $CD25^+$ $CD4^+$ T Regulatory Cells Suppress Naive and Memory T Cell Proliferation and Can Be Expanded In Vitro without Loss of Function*, J. Exp. Med., vol. 193, No. 11 (Jun. 4, 2001), pp. 1295-1301.
Dieckmann, D. et al., *Ex Vivo Isolation and Characterization of $CD4^+$ $CD25^+$ T Cells with Regulatory Properties from Human Blood*, J. Exp. Med., vol. 193, No. 11 (Jun. 4, 2001), pp. 1303-1310.
Taams, L. et al., *Human anergic/suppressive $CD4^+$ $CD25^+$ T cells: a highly differentiated and apoptosis-prone population*, Eur. J. Immunol., vol. 31 (2001), pp. 1122-1131.
Stephens, L. et al., *Human $CD4^+$ $CD25^+$ thymocytes and peripheral T cells have immune suppressive activity in vitro*, Eur. J. Immunol., vol. 31 (2001), pp. 1247-1254.
Baecher-Allan, C. et al., *$CD4^+$ $CD25^{high}$ Regulatory Cells in Human Peripheral Blood*, The Journal of Immunology, vol. 167 (2001), pp. 1245-1253.
Groux, H. et al., *A $CD4^+$ T-cell subset inhibits antigen-specific T-cell responses and prevents colitis*, Nature, vol. 389 (Oct. 16, 1997), pp. 737-742.
Extended European Search Report in European Application No. 10 01 4371.
Wang J, et al., "Inhibition of midkine alleviates experimental autoimmune encephalomyelitis through the expansion of regulatory T cell population", Proc Natl Acad Sci U S A. Mar. 11, 2008;105(10):3915-20.
Muhaimin Rifa'I et al.; "Essential Roles of $CD^+CD122^+$ Regulatory Cels in the Maintenance of T Cell Homeostasis"; J. Exp. Med.; vol. 200, No. 9; pp. 1123-1134; (2004).

\* cited by examiner

METHODS FOR TREATMENT OR PREVENTION OF DISEASES ASSOCIATED WITH FUNCTIONAL DISORDER OF REGULATORY T CELLS

This application is a divisional of U.S. application Ser. No. 12/084,907, filed Sep. 10, 2009, which is a national stage application of International application No. PCT/JP2006/322659, filed Nov. 14, 2006.

FIELD OF THE INVENTION

The present invention pertains to methods for expanding a regulatory T cell population and/or for therapy, prevention or diagnosis of diseases associated with the functional disorder of regulatory T cells and/or a method for screening a drug composition for the treatment or prevention of disease associated with the functional disorder of regulatory T cells.

RELATED ART

Midkine (hereinafter may be abbreviated as MK) is a member of the heparin-binding growth factor family, and is a non-glycosylated protein found to be the product of a gene responsive to retinoic acid. Its receptor is believed to be a complex consisting of receptor-type protein tyrosine phosphatase zeta, LRP (low-density lipoprotein receptor-related protein), ALK (anaplastic leukemia kinase), integrin and syndecan. MK is known to have cell migratory and angiogenic activity, as well as diverse bioactivity in canceration and inflammation; there have also been reports of overexpression of MK in the numerous cancerous tissues such as gastric cancer, colon cancer and breast cancer (non-patent references 1 and 2). Meanwhile, there have also been reports of intimal disorders and ischemic renal disease in MK-deficient mice (non-patent references 3 and 4).

In recent years, it has been indicated that MK may cause inflammatory cell migration and osteoclast differentiation, and may playing an important role in rheumatic diseases (non-patent references 5 and 6); however, the role of MK in immunological competence remains unknown.

T cells are one of the group of cells that play a central role in the immune system that defends the body against various pathogens. T cells can be roughly divided into CD4-positive helper T cells and CD8-positive cytopathic T cells. CD4-positive helper T cells can be classified in accordance with their cytokine-production pattern in specific stage of mature differentiation following antigen stimulation into such as Th1 cells and Th2 cells, which primarily produce IFN-gamma and IL-4, respectively. In general, Th1 cells and Th2 cells relate to biological defense, in the form of cell-mediated immunity and in the form of antibody-mediated immunity, respectively. The immune response relates to the elimination of pathogens and the acquirement of resistance to infection under a delicate balance through the functions of T cells of different characteristics. Normally, a healthy immune response mechanism eliminates foreign non-self antigens. At the same time, immunological tolerance keeps the elimination mechanism from functioning against autoantigens which are component within the body. As mentioned above, the body distinguishes between self and non-self antigens, and possesses a mechanism that eliminates only non-self antigens. In autoimmune diseases, this immunological homeostasis function is lost and the resultant hyperimmune response to self antigen causes the diseases.

The mechanisms by which various immunological tolerances are derived at the T cell level are known. One is the mechanism of eliminating autoreactive T cell clones in the thymus, known as central tolerance. The central tolerance comprises positive selection, through which only those cells that recognize Major Histocompatibility Complex are able to survive; and negative selection, through which cells that react strongly to autoantigens presented by thymocytes are eliminated. Another one is extrathymic control of autoreactive T cells through a mechanism known as peripheral tolerance. Peripheral tolerance mechanisms include inducement of cell death or nonresponsiveness to autoantigens, as well as active control by regulatory T cells (non-patent reference 7).

The regulatory T cells are new concept that has been proposed in recent years, and is defined to have inhibitory action against other T cells (non-patent reference 8). The immune response comprises a delicate balancing act, for example, Th1 cells and Th2 cells work antagonistically each other against their respective immune responses, and one works as the regulatory T cell to the other. There remains much room for argument about the verification of the existence of a cell population of regulatory T cells and the analysis of their nature. These regulatory T cells are studied in vitro or in vivo as cells having the function of inhibiting or adjusting specific immune responses, and have been reported as various cell populations by type of cell surface marker or cytokine produced, or by mechanism of inhibition or adjustment (non-patent reference 9).

Among these regulatory T cells, the most studied cell population is the CD4-positive, CD25-positive regulatory T cell population. Removal of CD25-positive, RT6.1-positive, CD5-positive, CD45RB-positive, CD45RC-positive, etc. cells from CD4-positive splenocytes of normal mice and rats, and the infusion of remaining T cells into T cell- and B cell-deficient SCID mice and rats induce organ-specific autoimmune diseases such as thyroiditis, gastritis, insulin-dependent autoimmune diabetes and colitis (non-patent references 10 and 11). Furthermore, insertion of CD25-negative CD4-positive cells into nude mice give rise to organ-specific autoimmune diseases, and insertion of peripheral CD4-positive, CD25-positive cells together with CD25-positive, CD4-positive, CD8-negative thymocytes suppresses the development of disease. These studies have contributed to the understanding that CD4-positive, CD25-positive regulatory T cells play an extremely important role in maintaining auto-tolerance.

It is known that similar CD4-positive, CD25-positive regulatory T cells are present in humans as well (non-patent references 12, 13, 14, 15, 16 and 17). CD4-positive, CD25-positive T cells isolated from human peripheral blood express CD45RO-positive memory T cell markers, and their expression level of activation markers such as HLA-DR is higher than that of CD4-positive, CD25-negative T cells. Furthermore, CTLA-4 is expressed steadily in the CD4-positive, CD25-positive cells and the expression level of CTLA-4 increases by stimulation. CD4-positive, CD25-positive T cells do not promote DNA synthesis or cytokine production after stimulation such as anti-CD3 antibody stimulation, stimulation by anti-CD3 and anti-CD28 antibodies or stimulation by allogeneic mature dendritic cells which indicates nonresponsiveness of the cells to antigenic stimulation. The addition of cytokines such as IL-2, IL-4 and IL-15 to the stimulation by anti-CD3 and anti-CD28 antibodies increases the DNA synthesize ability of CD4-positive, CD25-positive T cells, but does not change that ability of CD4-positive, CD25-negative T cells. The stimulation of CD4-positive, CD25-negative T cells by anti-CD3 antibodies or allogeneic mature dendritic cells in the presence of CD4-positive, CD25-positive T cells showed more anti-increasing in number effect dependent on the number of CD4-positive, CD25-positive T cells than the same stimulation in the absence of CD4-positive, CD25-positive T cells. There have been reports that while CD4-positive, CD25-positive T cells were able to produce inhibitory cytokines such as IL-10 and TGF beta1, the anti-increasing in number effect against CD4-positive, CD25-negative T cells is not lost by the neutralizing antibodies against these cytokines, and that the anti-increasing in number effect required direct intercellular contact between CD4-positive, CD25-negative T cells and CD4-positive, CD25-positive T cells. As mentioned above, there have been reports on the existence of CD4-positive, CD25-positive regulatory T cells in humans, and their properties has been investigated, but there has yet to be a fully detailed explanation of the mechanisms of their differentiation and inhibition.

There have also been reports regarding regulatory T cells that are induced by repeated stimulation by allogeneic antibodies and/or allogeneic immature dendritic cells in the presence of IL-10 in mice and humans (non-patent references 18 and 19). Unlike Th1 and Th2 cells, these cells are called Tr1 cells and characterized by high production of IL-10; moderate production of TGF-beta1, IFN-gamma and IL-5; low production of IL-2; and no production of IL-4. Similar to CD4-positive, CD25-positive regulatory T cells, Tr1 cells are nonresponsive, while the mechanism to suppress T cells can be partially explained by the IL-10 and TGF-beta1 produced by the Tr1 cells. However, it is not all clear whether Tr1 cells and CD4-positive, CD25-positive regulatory T cells are completely different subsets of T cells, or are different differentiation/activation stages of the same cell population.

In the X-linked recessive inheritance disorder called IPEX, there is a high incidence of inflammatory colitis, allergies and organ-specific autoimmune diseases such as insulin-dependent diabetes and thyroiditis. The gene which causes this disorder is believed to be FOXP3. It is known that FOXP3 is selectively expressed in CD4-positive, CD25-positive regulatory T cells. Also, it appears that the expression of FOX3 gene in other T cells can functionally convert the T cells into CD4-positive, CD25-positive regulatory T cells. Furthermore, mice with abnormal FOXP3 gene developed serious autoimmune disorders, and the disorders were prevented by the infusion of CD4-positive, CD25-positive regulatory T cells prepared from normal mice (non-patent reference 20).

It is known that CD4-positive, CD25-positive regulatory T cells are deeply correlated with multiple sclerosis. Patients with relapsing-remitting multiple sclerosis (RRMS) had a notably reduced amount of CD4-positive, CD25-positive regulatory T cells (non-patent references 21, 22 and 23). Also, in studies using the experimental autoimmune encephalomyelitis (EAE) mouse model, which is considered to be a model of multiple sclerosis, it has been reported that CD4-positive, CD25-positive regulatory T cells inhibit development of EAE as well as the increase in number of T cells and the production of IFN-gamma against myelin oligodendrocyte glycoprotein (MOG) (non-patent references 24, 25 and 26). Myasthenia gravis (MG) is believed to be a CD4-positive T cell-dependent autoimmune disease, and it has been reported that patients with myasthenia gravis have functional abnormality of CD4-positive, CD25-positive regulatory T cells and reduced FOXP3 expression (non-patent reference 27). CD4-positive, CD25-positive regulatory T cells are also correlated with inflammatory bowel disease (IBD) and Crohn's disease. Infusion of CD4-positive, CD45RBhigh T cells into immunodeficient mice causes Th1 cell-induced colitis. On the other hand, concomitant infusion of CD4-positive, CD25-positive regulatory T cells with CD4-positive, CD45RBhigh T cells does not cause colitis (non-patent references 28 and 29).

There have also been numerous studies on the correlation of CD4-positive, CD25-positive regulatory T cells with rheumatoid arthritis (RA) and systemic lupus erythematosus (SLE). It has been reported that from analysis of regulatory T cells in the peripheral blood of 23 subjects with SLE (19 active and 4 inactive), 15 subjects with RA and 27 healthy subjects, the number of CD4-positive, CD25-positive regulatory T cells showed no difference among the SLE subjects, RA subjects and healthy subjects, but the suppressive function of the cells was greatly reduced among the SLE subjects and RA subjects compared to the healthy subjects (non-patent reference 30). It is also known that CD4-positive, CD25-positive regulatory T cells are correlated with type I diabetes (non-patent reference 31), transplant rejection reaction (non-patent reference 32) and cancer (non-patent reference 33).

CD4-positive, CD25-positive regulatory T cells are a rare cell population, accounting for only 5 to 10% of CD4-positive T cells in peripheral blood, and are nonresponsive to activation stimuli. Cell increase can be promoted by adding cytokines such as IL-2, IL-4 and IL-15 to the stimulation by anti-CD3 antibodies and anti-CD28 antibodies. It is anticipated that increase of the number of CD4-positive, CD25-positive regulatory T cells will be applied to the treatment of autoimmune diseases, transplants and allergies.

Multiple sclerosis (hereinafter may be abbreviated as MS) is an autoimmune disease that causes inflammatory demyelination in the central nervous system. It has been assumed that various immune cells play a role in the disease, but the true nature of the disease has yet to be understood. In recent years, it has been indicated that regulatory T cells (CD4-positive, CD25-positive, FOXP3-positive T cells) inhibitory regulate MS disease condition. CD4-positive, CD25-positive regulatory T cells regulate autoimmune expression by maintaining immunological tolerance. Thus, it is believed that the functional abnormality of these cells contributes to the pathgenesis of various autoimmune diseases, but the details of this mechanism remain to be elucidated.

DISCLOSURE OF THE INVENTION

Problems to be Solved by the Invention

The present invention was developed in consideration of the situation described above, and the aim of the invention is to provide a method for expanding a regulatory T cell population. The other aim of the invention is to provide a method of therapy, prevention or diagnosis for diseases associated with the functional disorder of regulatory T cells.

Means to Solve the Problems

It was discovered that the number of CD4-positive, CD25-positive regulatory T cells had increased in Midkine (MK)-deficient mice, and that administration of MK reduced the number of CD4-positive, CD25-positive regulatory T cells. In addition, the following results were from their study of experimental autoimmune encephalomyelitis (hereinafter may be abbreviated as EAE), which is a model of multiple sclerosis.

First, inducement of EAE to the MK-deficient mice showed mitigation of clinical symptoms (FIG. 1). This effect was eliminated by the treatment with MK (FIG. 1).

Next, the dynamics of CD4-positive, CD25-positive regulatory T cells in said EAE model animals were examined to investigate the role of MK in EAE expression and CD4-positive, CD25-positive regulatory T cell function. Since EAE is a disease induced by type 1 helper T cells (Th1), the Th1/Th2 balance in MK-deficient mice was also investigated to examine the effect of MK on the Th1/Th2 balance.

The results of these studies indicated that changes in the CD4-positive cells which induce the disease were not responsible for the mitigation of clinical symptoms in these model animals (FIG. 2), but an increase in the number of CD4-positive, CD25-positive regulatory T cells were responsible for the mitigation (FIGS. 3 and 4). In addition, EAE inducement in MK-deficient mice led an increased number of CD4-positive, CD25-positive cells compared to the EAE inducement in wild type mice, and administration of MK decreased the number of CD4-positive, CD25-positive cells (FIG. 5). Furthermore, an increase in the number of these CD4-positive, CD25-positive regulatory T cells inhibited type 1 helper T cells, which induce cell-mediated immunity (FIG. 6).

Next, the effect of treatment with anti-MK antibodies, which is one of the MK inhibitor, on CD4-positive, CD25-positive regulatory T cell dynamics in EAE model mice was analyzed. The results indicated that treatment with the MK inhibitor mitigated clinical symptoms (FIG. 8). Specifically, there was delayed onset and reduced severity of the disease in the mice immunized with MOG35-55 and then had been treated with anti-MK antibodies (FIG. 8).

Furthermore, the inventors treated the EAE model mice with an anti-MK aptamer, an MK inhibitor, and the clinical symptoms were observed. The results indicated mitigation of clinical symptoms similar to that of the treatment with anti-MK antibodies (FIG. 9).

In other words, MK has the effect of inhibiting the increase in number of regulatory T cells and function of regulatory T cells, and that inhibition of MK expression or activity can eliminate the MK's inhibitory effect to the increase and function of regulatory T cells, as overviewed above, the inventors achieved the present invention. The inventors discovered that anti-MK aptamer can have a suitable inhibitory effect.

More specifically, the present invention provides (1) through (10) below.

(5) A method as set forth in (3) or (4), wherein the disease associated with the functional disorder of regulatory T cells is an autoimmune disease, allergic disease, chronic transplant rejection, thyroid abnormality, inflammatory colitis, type 1 diabetes, multiple sclerosis, myasthenia gravis, rheumatoid arthritis, systemic lupus erythematosus, or amyotrophic lateral sclerosis.

(1) A method for increasing the number of regulatory T cells comprising of inhibition of MK using an aptamer against MK.

(2) A method for increasing the number of regulatory T cells comprising of administration of an aptamer against MK, which is a MK inhibitor.

(3) A method for the treatment or prevention of disease associated with the functional disorder of regulatory T cells comprising of inhibition of MK using an aptamer against Midkine.

(4) A method for the treatment or prevention of disease associated with the functional disorder of regulatory T cells comprising of administration of a MK inhibitor which is an aptamer against Midkine.

(6) A method for screening a medicament for the treatment or prevention of disease associated with the functional disorder of regulatory T cells by binding to the expressed MK, comprising:

(a) a step of contacting a test compound to MK;
(b) a step of detecting said binding between MK and a test compound; and
(c) a step of selecting the compound which binds to MK;

wherein the medicament that binds the expressed MK comprises an aptamer against midkine.

(7) A method according to claim 6, wherein the disease associated with the functional disorder of regulatory T cells is an autoimmune disease, allergic disease, chronic transplant rejection, thyroid abnormality, inflammatory colitis, type 1 diabetes, multiple sclerosis, myasthenia gravis, rheumatoid arthritis, systemic lupus erythematosus, or amyotrophic lateral sclerosis.

(8) A method of diagnosis for diseases associated with the functional disorder of regulatory T cells comprising a substance that binds to Midkine, which substance comprises an aptamer against Midkine.

(9) A method as set forth in (8), wherein the disease associated with the functional disorder of regulatory T cells is an autoimmune disease, allergic disease, chronic transplant rejection, thyroid abnormality, inflammatory colitis, type 1 diabetes, multiple sclerosis, myasthenia gravis, rheumatoid arthritis, systemic lupus erythematosus, or amyotrophic lateral sclerosis.

BRIEF EXPLANATION OF DRAWINGS

FIG. 6A indicates the quantities of IFN-gamma and FIG. 6B indicates the quantities of IL-4 that are present in the culture supernatant of CD4-positive T cells that had been purified from murine splenocytes and cultured in the presence of $MOG_{35-55}$ (20 µg/mL). The values are expressed as mean±SEM for five mice. The Y-axis unit is pg/mL. The p value is calculated in accordance with the student t-test.

BEST MODE FOR CARRYING OUT THE INVENTION

Figure 1:
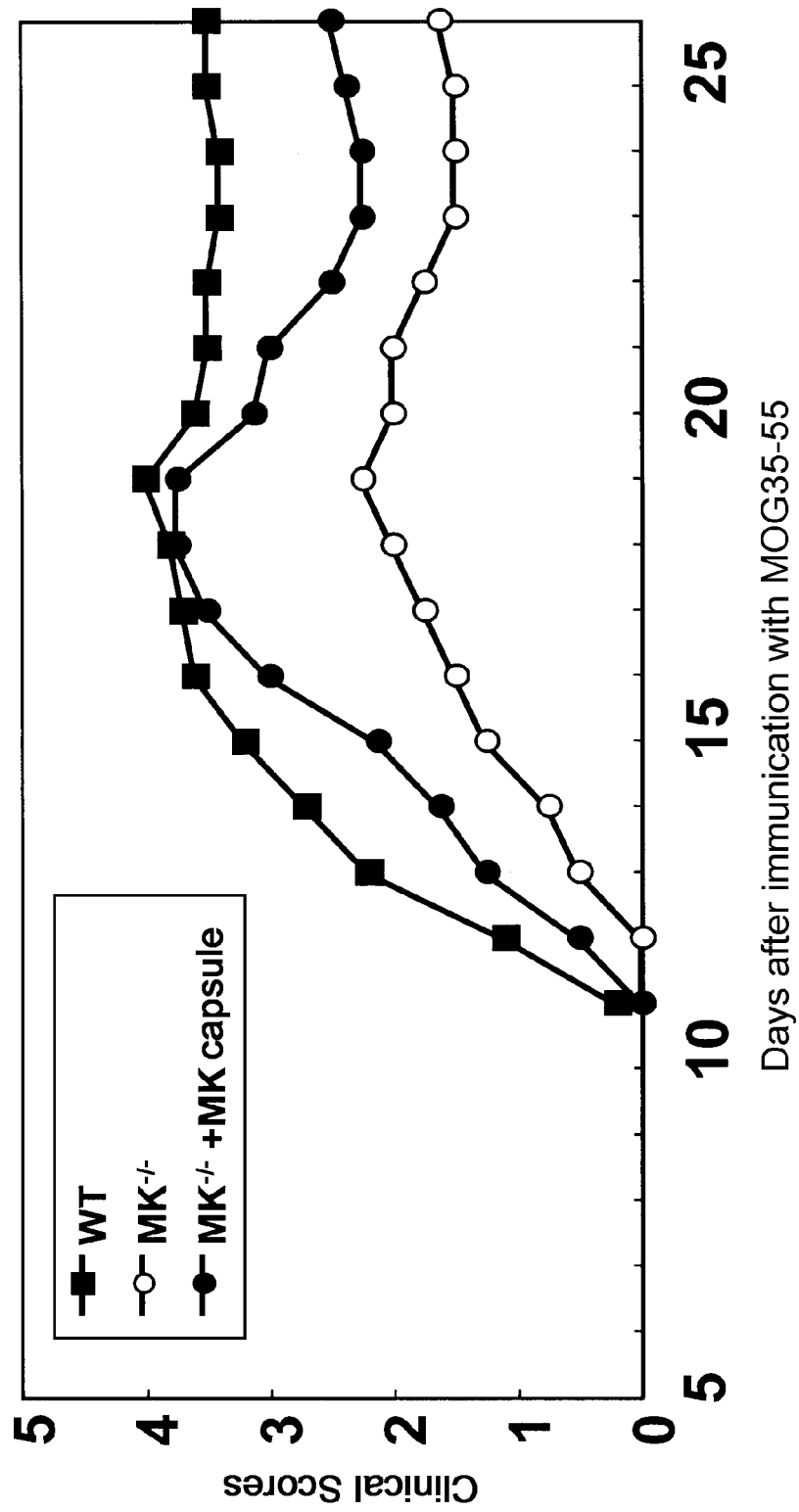
FIG. 1 The figure indicates the results of observation of clinical symptoms in wild-type mice (C57BL-6), MK-deficient mice and MK-deficient mice treated with MK, in which experimental autoimmune encephalomyelitis had been induced. The mean values for all animals to day 25 following immunization are shown. A curve is drawn in accordance with the Kaplan-Meier method.

MK has the effect of inhibiting the increase in number of regulatory T cells and function of regulatory T cells, and that inhibition of MK expression or activity can eliminate the inhibitory activities. The present invention is based on these findings.

The present invention pertains to a therapeutic or preventive agent for diseases associated with the functional disorder of regulatory T cells comprising an aptamer against MK.

In the present invention, the term "aptamer" refers to nucleic acids that bind to various molecules such as proteins and hormones. The term, MK aptamer or aptamer against MK refers to nucleic acids that bind to MK. The term, MK aptamer inhibitor refers to nucleic acids that bind to MK, thereby inhibiting the MK from binding to molecules that bind to MK, such as MK receptors and extracellular matrices. MK aptamers may be RNA or DNA; there are no particular limitations to the RNA and DNA as long as it binds to MK. Nucleic acids, whose ribose, phosphate backbone, nucleic acid base, or/and 5' or/and 3' end has been modified, may be included in said RNA and DNA, and; there is no limitation as long as these nucleic acids bind to MK. The nucleic acid chain may be single- or double-stranded, but single-stranded chain is preferable.

There is no limitation to the length of the aptamer, as long as it is long enough to bind specifically to the target molecule; however, they may consist of 10 to 200 nucleotides, preferably 10 to 100 nucleotides, more preferably 15 to 80 nucleotides, and the most preferably 15 to 50 nucleotides.

Aptamers comprising nucleotides alone can be used as a therapeutic agent, and also those bound to other molecules, such as polyethylene glycol, cholesterol, peptides, liposome, fluorescent pigment, radioactive substance, toxin or another aptamer, can be used. In the present invention, the term "aptamer" includes such aptamers to which other molecules are bound.

Aptamers in the present invention can be selected utilizing methods known well by a person skilled in the art. It is not intended to limit the method, but aptamers can be selected by, for example, the SELEX method (systematic evolution of ligands by exponential enrichment) (Tuerk, C. and Gold, L., 1990, Science, 249: 505-510). The SELEX method is a method wherein a nucleic acid pool having approximately 10<15> different nucleotide sequences, is mixed with a target substance, and then nucleic acids that bind to or strongly bind to the target substance are selected. The selected nucleic acids are amplified by RT-PCR or PCR, and are used as the template for the next round. Approximately ten repetitions of these steps yield the target aptamers. When using aptamers as a drug, minimizations in size and stabilization are required. Practically, they can be minimizing in size by eliminating nucleotides that have no effect on their activity, and can be stabilized by modification. The half life of natural RNA in serum is several seconds, however, the half life can be extended to one week or longer by, for example, O-methylation on the 2'-position of ribose and binding inverted dT to the both ends of the RNA.

The term "treatment or prevention of diseases associated with the functional disorder of regulatory T cells" in the present invention refers to the inhibition or prevention of symptoms of diseases associated with the functional disorder of regulatory T cells, and/or symptoms of complicating diseases associated with the functional disorder of regulatory T cells. The term "diseases associated with the functional disorder of regulatory T cells" in the present invention refers to diseases associated with the reduction in the number of regulatory T cells in the body, or diseases associated with the reduced functioning of regulatory T cells. "Diseases associated with the functional disorder of regulatory T cells" in the present invention are preferably diseases that are associated with the functional abnormality of CD4-positive, CD25-positive regulatory T cells.

Examples of diseases associated with the functional abnormality of regulatory T cells include multiple sclerosis, autoimmune diseases, allergic diseases, chronic transplant rejection, inflammatory colitis, type 1 diabetes, amyotrophic lateral sclerosis, chronic rheumatoid arthritis, systemic lupus erythematosus (SLE), myasthenia gravis, progressive systemic sclerosis (PSS), Sjögren's Syndrome, polymyositis (PM), dermatomyositis (DM), polyarteritis nodosa (PN), thyroid abnormality, Graves' disease, Guillian-Barre Syndrome, primary biliary cirrhosis (PBC), idiopathic thrombocytopenic purpura, autoimmune hemolytic anemia in inflammatory colitis, and Crohn's disease, and are preferably autoimmune diseases, allergic diseases, chronic transplant rejection, inflammatory colitis, type 1 diabetes, multiple sclerosis, amyotrophic lateral sclerosis and myasthenia gravis. Multiple sclerosis can be one of the preferable diseases which are treated in the present invention.

The "an expansive agent for regulatory T cell population" or "therapeutic or preventive agent for diseases associated with the functional disorder of regulatory T cells" of the present invention is effective particularly against the above-mentioned diseases which are diagnosed as being caused by the reduction of the number of regulatory T cells.

The an expansive agent for regulatory T cell population and therapeutic or preventive agent for diseases associated with the functional disorder of regulatory T cells of the present invention may include pharmacologically acceptable excipients such as preservatives and stabilizers. Such pharmacologically acceptable excipients can be excipients that are pharmacologically permissible and can be administered with the above-mentioned an expansive agent for regulatory T cell population and/or therapeutic agent, wherein the excipients themselves have the above-mentioned increasing effect for regulatory T cells or therapeutic effect against diseases associated with the functional abnormality of regulatory T cells, or wherein the excipients which do not have said increasing effect or therapeutic effect. The excipients may not have the above-mentioned increasing effect for regulatory T cells or therapeutic effect against diseases associated with the functional abnormality of regulatory T cells, but may have a synergistic or additive stabilizing effect when used concomitantly with an aptamer against MK.

For example, pharmacologically acceptable ingredients include sterilized water, physiological saline solution, stabilizers, fillers, buffering agents, preservatives, surfactants, chelating agents (e.g., EDTA) and binders.

Surfactants used with the aptamer against MK include nonionic surfactants, for example, sorbitan fatty acid esters, such as sorbitan monocaprylate, sorbitan monolaurate and sorbitan monopalmitate; and glycerin fatty acid esters with an HLB value of 6 to 18, such as glycerin monocaprylate, glycerin monomyristate and glycerin monostearate.

The surfactants may also be anionic surfactants. These include alkylsulfates having an alkyl group of 10 to 18 carbon atoms, such as sodium cetylsulfate, sodium laurylsulfate and sodium oleylsulfate; polyoxyethylene alkylethersulfate salts having an alkyl group of 10 to 18 carbon atoms whose mean number of moles of added ethyleneoxides is 2 to 4, such as sodium polyoxyethylene laurylsulfate; an alkylsulfosuccinate ester salt whose alkyl group has 8 to 18 carbon atoms, such as sodium laurylsulfosuccinate ester; natural surfactants, such as lecithin and glycerophospholipid; sphingophospholipids such as sphingomyelin; and sucrose fatty acid esters whose fatty acids have 12 to 18 carbon atoms.

One or a combination of two types of these surfactants may be added to the aptamer against MK. Preferable surfactants used in the formulation of the composition of the present invention are polyoxyethylene sorbitan fatty acid esters, such as polysorbate 20, 40, 60 or 80; preferably polysorbate 20 and 80. Polyoxyethylene polyoxypropylene glycols, such as poloxamer (such as Pluronic F68 (Registered Trademark)) are also preferable.

Buffering agents used with the aptamer against MK include phosphoric acid, citric acid buffer solution, acetic acid, malic acid, tartaric acid, succinic acid, lactic acid, potassium phosphate, gluconic acid, caprylic acid, deoxycholic acid, salicylic acid, triethanolamine, fumaric acid, and other organic acids; and carbonate buffer solution, tris buffer solution, histidine buffer solution, and imidazole buffer solution.

Solution formulations of the aptamer against MK may be prepared by dissolving the aptamer in an aqueous buffer solution known well in the field of solution formulation. The concentration of the buffer solution is generally 1 to 500 mM, preferably 5 to 100 mM, and more preferably 10 to 20 mM.

The aptamer against MK may also be administered with other ingredients such as polypeptides of low molecular weight, serum albumin, proteins such as gelatin and immunoglobulin, amino acids, sugars and carbohydrates such as polysaccharides and monosaccharides, and sugar alcohols.

For example, sugars and carbohydrates such as polysaccharides and monosaccharides of the present invention include dextran, glucose, fructose, lactose, xylose, mannose, maltose, sucrose, trehalose and raffinose.

For example, sugar alcohols useful in the present invention include mannitol, sorbitol and inositol.

The aptamer may be administered in a pharmaceutical composition in the formulation of an injectable aqueous solution, optionally including solvents such as physiological saline solution, isotonic solutions containing glucose or other adjuvants, such as D-sorbitol, D-mannose, D-mannitol and sodium chloride. Suitable solubilizing agents such as alcohol (e.g., ethanol), polyalcohol (e.g., propylene glycol and PEG) and nonionic surfactants (e.g., polysorbate 80, HCO-50) may be used concomitantly. The aptamer may also be formulated with diluents, solubilizing agents, pH adjusters, soothing agents, sulfur-containing reducing agents, antioxidants, etc. if desired.

Furthermore, the aptamer may be contained in microcapsules (micro capsules formed of hydroxymethylcellulose, gelatin, poly[methylmethacrylic] acid, etc.), or may be delivered in the form of a colloidal drug delivery system (liposome, albumin microsphere, microemulsion, nanoparticles, nanocapsules, etc.) if needed (see Remington's Pharmaceutical Science 16th Edition, Oslo Ed., 1980, etc.). Methods for forming sustained-release formulation are also well known, and may be applied to the present invention (Langer et al., J. Biomed. Mater. Res. 1981, 15: 167-277; Langer, Chem. Tech. 1982, 12: 98-105; U.S. Pat. No. 3,773,919; European patent application laid-open numbers EP58481 and EP133988; Sidman et al., Biopolymers 1983, 22: 547-556). Pharmacologically permissible carriers to be used may be selected from the above-mentioned list depending on the form of the drug, either singly or in combination, but are not limited thereto.

The aptamer is said to be an inhibitor of midkine. The biological and biochemical functions of MK that may be inhibited include one or more of promotion of cell proliferation (promotion of fibroblast, keratinocyte or tumor cell proliferation), enhancement of cell survival (enhancement of survival of fetal neurons or tumor cells), promotion of cell migration (promotion of neuron, neutrophil, macrophage, osteoblast or vascular smooth myocyte migration), promotion of chemokine expression, promotion of angiogenesis and promotion of synapse formation. Biological properties include specificity of expression-site and expression level.

The MK aptamer can be effective against MK derived from, but not limited to, humans, monkeys, mice, rats, guinea pigs, pigs, cows, yeast and insects.

The present invention pertains to use of a midkine inhibitor that is an aptamer against midkine in the manufacture of a medicament for treating or preventing diseases associated with the functional disorder of regulatory T cells, including steps of inhibiting MK expression or activity in cells that express MK using an aptamer against MK. In the present invention, the number of regulatory T cells may be increased or the number of type 1 helper T cells may be reduced by inhibiting MK expression or activity using an aptamer against MK.

The expression "inhibit MK expression" in the present invention includes the inhibition of gene transcription as well as the inhibition of translation into a protein. It also includes not only the complete termination of DNA expression, but also the reduction of its expression.

When using the MK inhibitor of the present invention as a drug for humans or other animals, it is possible to administer these compounds directly to patients or to administer them after formulation by using well known pharmacological methods. The above-mentioned pharmacologically acceptable excipients may be added for formulation purposes.

The aptamer against midkine can be administered in the form of a drug, either systemically (orally or non-orally), or locally. Administration routes include intravenous injection such as intravenous drip, intramuscular injection, intraperitoneal injection, subcutaneous injection, suppository, enema and oral enteric coating drug. The administration route can be selected appropriately depending on the age and symptoms of the patient. The effective dosage is selected from the range of 0.001 mg to 100 mg per kg of body weight. Alternatively, a dosage of 0.1 to 1000 mg, preferably 0.1 to 50 mg per patient can be selected. For an MK aptamer, the effective dosage level is that the free aptamers are found in the blood. Specifically, for example, the preferable dosage and administration is a dose of 0.1 mg to 100 mg, preferably 0.1 mg to 40 mg per kg of body weight per month (4 weeks), either in a single dose or divided into several doses, e.g., twice weekly, once weekly, once biweekly, or once every four weeks, by intravenous injection such as intravenous drip, or subcutaneous injection.

EXAMPLES

Examples of the present invention are explained as follows, however, the present invention is not limited to following examples.

Example 1

Inducement of Experimental Autoimmune Encephalomyelitis in MK-Deficient Mice, and Observation of Clinical Symptoms First, experimental autoimmune encephalomyelitis was induced in MK-deficient mice, and their clinical condition was observed. Eight- to ten-week-old wild-type and MK-deficient C57BL-6 mice (provided by Dr. Muramatsu, Nagoya University, Japan; Nakamura, E., et al., Genes Cells 3: 811-822 (1998)) were inoculated with 300 g of myelin oligodendrocyte glycoprotein peptide 35-55 (MOG35-55) (MEVGWYRSPFSRWHLYRNGK) (SEQ ID NO.: 3) that had been emulsified with 500 g of incomplete Freund's adjuvant containing killed *Mycobacterium tuberculosis*. Then EAE was induced in the mice by administering 300 ng of pertussis toxin dissolved in 200 L of PBS immediately after sensitization and 48 hours thereafter. The clinical symptoms of the animals were evaluated daily thereafter by the following standards (FIG. 1). Clinical scores were assigned daily to the wild-type mice (n=16) and MK-deficient mice (n=13) to evaluate the clinical symptoms. The clinical scores in FIG. 1 indicated 0: no symptoms; 1: loss of tail tone; 2: unsteady gait; 3: hind limb paralysis; 4: paralysis of four limbs; 5 death. The proportion of all animals was recorded for the first 25 days following inoculation.

The results indicated mitigation of clinical symptoms in MK-deficient mice (FIG. 1). Specifically, there was delayed disease onset and mitigation of severity of disease in MK-deficient mice after inoculation of MOG35-55.

Example 2

Examination of Effect of Administration of MK on the Clinical Symptoms Of Experimental Autoimmune Encephalomyelitis in MK-Deficient Mice MK-deficient mice in which experimental autoimmune encephalomyelitis had been induced, were treated with MK, and the effect of MK on the clinical symptoms were examined.

MK dissolved to 1 mg/mL was packed in a micro-osmotic pump (Model 1002, Durect Corp., Cupertino, Calif.) and administered intraperitoneally to MK-deficient mice. A total of 200 mg/day of MK was administered to the mice through this micro-osmotic pump, at a rate of 0.25 L per hour for 14 days, and their clinical symptoms were evaluated using the same method described in example 1 (n=13). PBS alone was administered intraperitoneally to the control group through the micro-osmotic pump. The results indicated that the effect of mitigating clinical symptoms in MK-deficient mice disappeared (FIG. 1).

Example 3

Pathologic Examination of Individual Mice

The spinal cord was removed from the mice in each of the groups in examples 1 and 2 after the onset of EAE (day 14 after sensitization), fixed in formalin, stained with hematoxylin-eosin by a well known method, and examined pathologically.

The results indicated a reduction of CNS inflammation in MK-deficient mice after MOG35-55 inoculation.

Example 4

Analysis of the Dynamics of CD4-Positive T Cells or CD4-positive, CD25-positive regulatory T cells in autoimmune encephalomyelitis model animals The role of MK in EAE expression and CD4-positive, CD25-positive regulatory T cell function was investigated by examining the dynamics of CD4-positive, CD25-positive regulatory T cells in said autoimmune encephalomyelitis model animals.

Lymphocytes were isolated from the spleen, mesenteric lymph nodes and popliteal lymph nodes of mice in the wild-type, MK-deficient and MK-dosed groups after EAE onset (12 to 14 days post-inoculation), and the numbers of CD4-positive, CD8-positive cells and CD4-positive, CD25-positive cells were assayed by flow cytometry.

Figure 2:
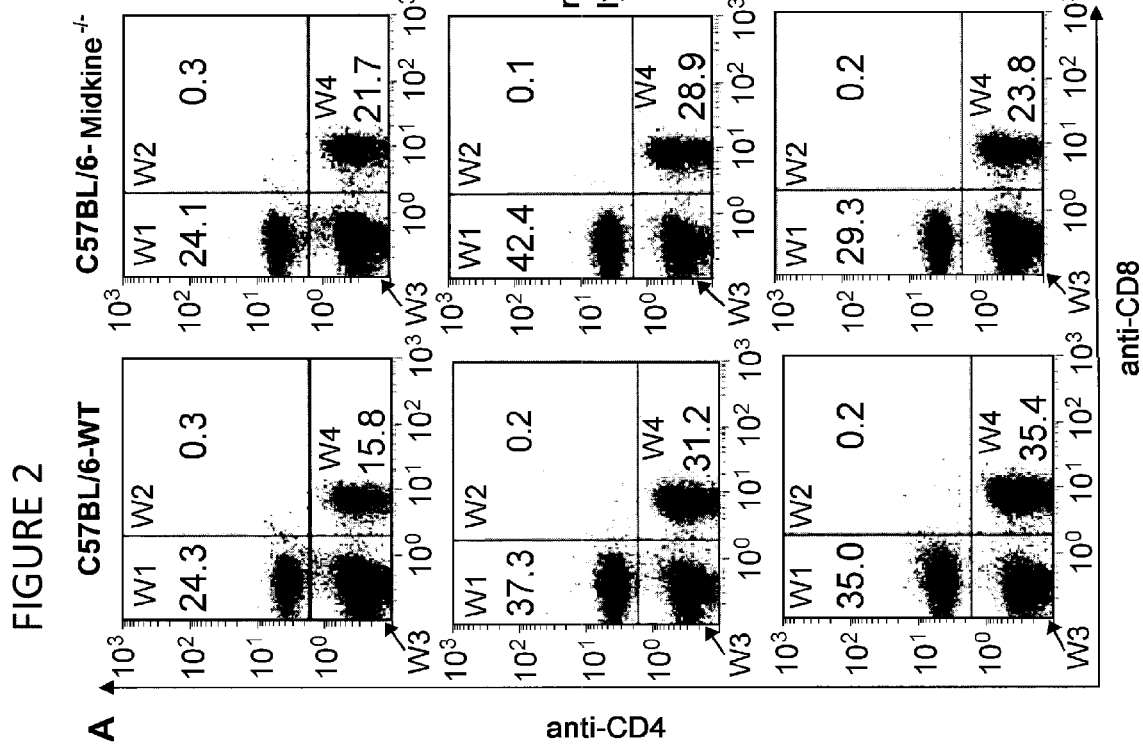
FIG. 2 The figure indicates the proportion of CD4-positive T cells in the peripheral lymph nodes of wild-type mice (C57BL-6) and MK-deficient mice following immunization with MOG35-55. Figure A indicates the in vivo ratio of CD4-positivie and CD8-positive cells in the spleen, mesenteric lymph nodes and popliteal lymph nodes of wild-type mice and MK-deficient mice. Figure B indicates the proportion of CD4-positive T cells among all mononuclear cells in the three sites mentioned above. The values are expressed as mean SEM. The p value was calculated in accordance with the student t-test.

The results indicated that there were no significant differences in the proportion of CD4-positive T cells between the peripheral lymph nodes of MOG35-55 inoculated wild-type mice and those of MK-deficient mice (FIG. 2). Meanwhile, there was increased activity of CD4-positive, CD25-positive T cells in the peripheral lymph nodes of MK-deficient mice (FIG. 3).

Next, the CD4-positive T cells were purified (>95% CD4-positive cells) through a magnetic cell sorter (MACS) and cultured in the presence of MOG35-55 (20 g/mL), and the proportion of CD4-positive, CD25-positive T cells was analyzed by flow cytometry. Practically, 1 mg/mL MK or PBS was administered to wild-type mice and MK-deficient mice through the micro-osmotic pump on the first day in the same manner as described in example 2, then 200 g/mouse of MOG35-55 was administered to them on the first day and two days thereafter. The CD4-positive T cells from the splenocytes of the mice at the peak of their clinical symptoms were purified, and said cells (2×10<5> cells per well) were cultured in vitro for four days in the presence of MOG35-55 (20 g/mL) and antigen-presenting cells (hereinafter abbreviated APC; splenocytes of normal mice treated with mitomycin C for 30 minutes at 37 deg. C.; 5×10<6> cells per well). After four days, the expression of CD4-positive, CD25-positive T cells was analyzed by FACS. Furthermore, cDNA from CD4-positive T cells purified through CD4 microbeads was prepared, and analyzed by real-time RT-RCR to determine the FOXP3 mRNA level.

Figure 4:
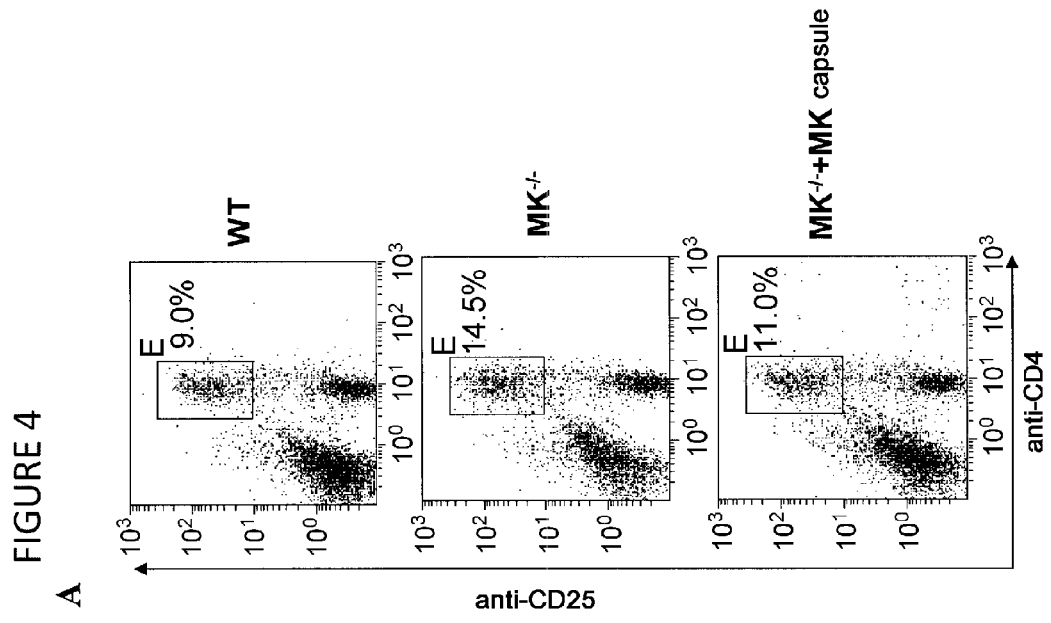
FIG. 4 The figure indicates the dynamics of CD4-positive, CD25-positive regulatory T cells in experimental autoimmune encephalomyelitis model animals. Figure A indicates the results of examining the proportion of spleen-derived CD4-positive T cells following stimulation with MOG35-55 in wild-type mice, MK-deficient mice, and MK-deficient mice treated with MK. Figure B indicates the results of analyzing FOXP3 mRNA expression in spleen-derived CD4-positive T cells from each of the above-mentioned groups by the real-time RT-PCR method following stimulation with MOG35-55. The figures indicate relative values to FOXP3 mRNA expression in standard CD4-positive T cells.

The results indicated that administration of MK to MK-deficient mice inhibited CD4-positive, CD25-positive T cell expression (FIG. 4).

Figure 3:
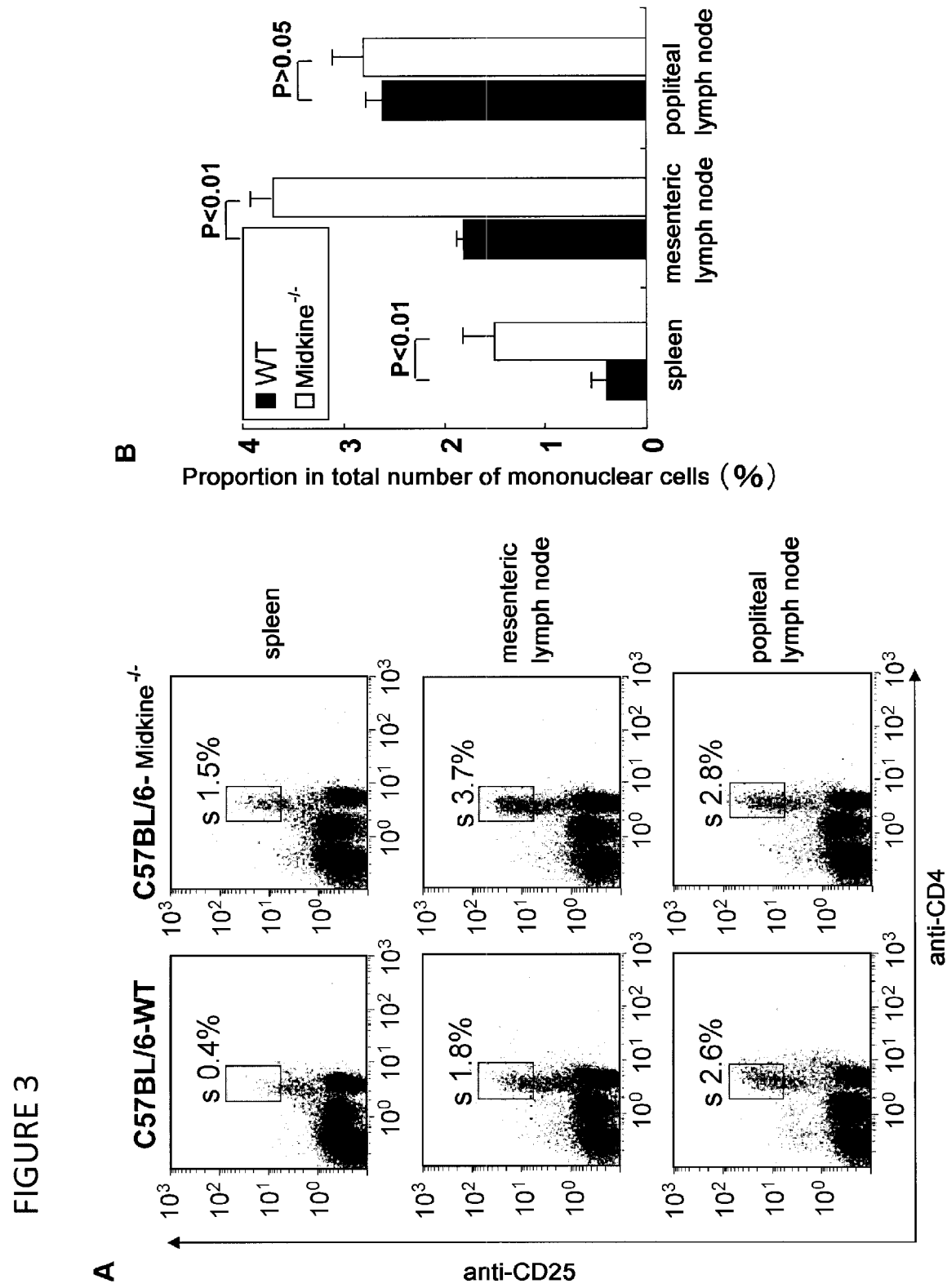
FIG. 3 The figure indicates the proportion of CD4-positive, CD25-positive T cells in the peripheral lymph nodes of wild-type mice (C57BL-6) and MK-deficient mice following immunization with MOG35-55. Figure A indicates the cytofluorescence characteristic of in vivo CD4-positive, CD25-positive T cells in the spleen, mesenteric lymph nodes and popliteal lymph nodes of wild-type mice and MK-deficient mice. Figure B indicates the proportion of CD4-positive, CD25-positive T cells among all mononuclear cells in the three sites mentioned above. The values are expressed as mean SEM. The p value is calculated in accordance with the student t-test.

The above results revealed that the mitigation of clinical symptoms in these model animals was associated not with changes in the CD4-positive cells that induce the disease (FIG. 2), but rather with the increase in the CD4-positive, CD25-positive regulatory T cells (FIGS. 3 and 4).

Example 5

Figure 5:
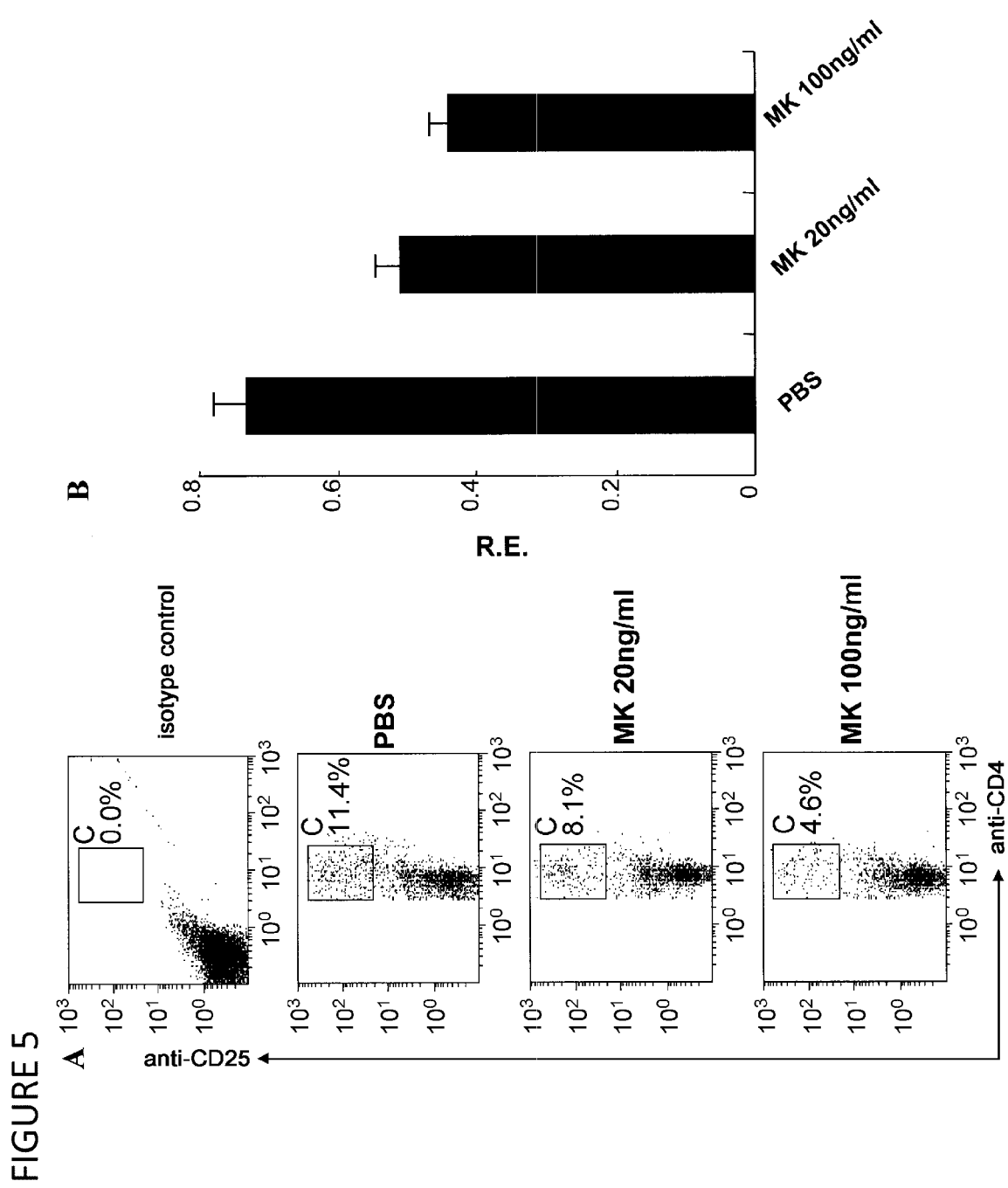
FIG. 5 The figure indicates the effect of the addition of MK on the dynamics of CD4-positive, CD25-positive T cells in MK-deficient mice. Figure A indicates the proportion of CD4-positive, CD25-positive regulatory T cells from each of the above-mentioned groups following stimulation of spleen-derived CD4-positive T cells with MOG35-55. The CD4-positive part was gated, and only the CD4-positive cells were analyzed. Figure B indicates the results of analyzing FOXP3 mRNA expression in spleen-derived CD4-positive T cells from each of the above-mentioned groups by the real-time RT-PCR method following stimulation with MOG35-55. The figures indicate values for GAPDH mRNA expression relative to FOXP3 mRNA expression.

Analysis of the Effect of the Addition of MK on the Dynamics Of CD4-Positive, CD25-Positive T Cells in MK-Deficient Mice Next, CD4-positive T cells derived from the spleen of MK-deficient mice were stimulated with MOG35-55 in the presence of 0, 20 and 100 ng/mL of MK, and the proportion of CD4-positive, CD25-positive T cells and FOXP3 mRNA expression were analyzed in the same manner as described in example 4. The results revealed that the proportion and expression of CD4-positive, CD25-positive T cells decreased in MK-deficient mice as the concentration of the MK added increased (FIG. 5).

Example 6

Analysis of the Th1/Th2 Balance in MK-Deficient Mice

Since EAE is a disease induced by type 1 helper T cells (Th1), the Th1/Th2 balance in MK-deficient mice and the effect of MK on the Th1/Th2 balance was examined.

Specifically, CD4-positive T cells from the splenocytes of the mice at the peak of their clinical symptoms of EAE were purified, and said cells (2×10<5> cells per well) were cultured in vitro for three days in the presence of MOG35-55 (20 g/mL) and APC. The IFN-gamma and IL-4 levels in the culture supernatant were assayed by ELISA.

Figure 6:
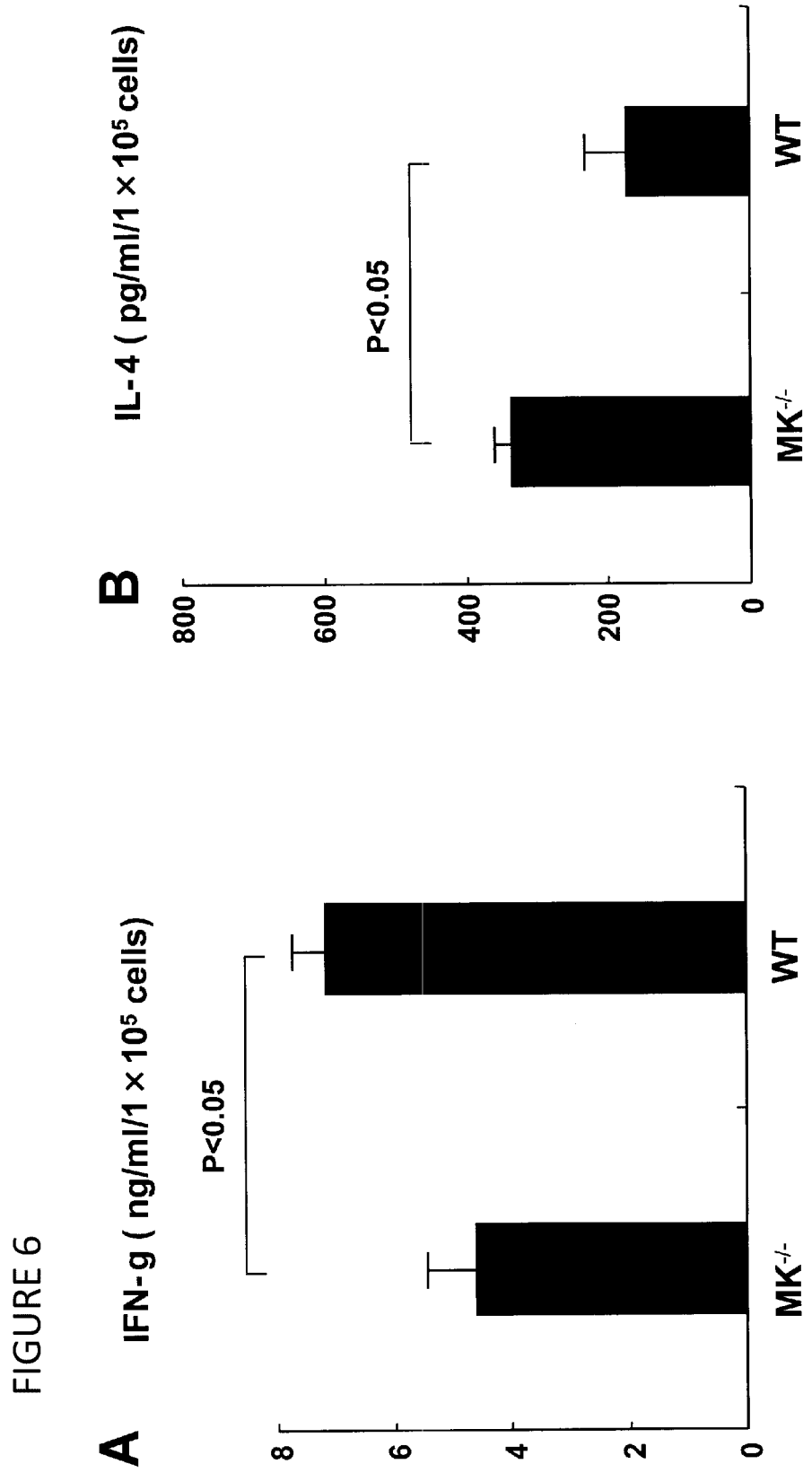
FIG. 6 The figure indicates the Th1/Th2 balance in MK-deficient mice.

The results revealed that type 1 helper cells, which induce cellular immunity, are also inhibited in midkine-deficient mice (FIG. 6).

Example 7

In Vitro Analysis of the Effect of the Addition of Anti-MK Antibodies on the Dynamics of CD4-Positive, CD25-Positive T Cells in EAE Model Mice Preparation of Murine Anti-Human MK Monoclonal Antibodies
(Preparation of MK Gene Knockout Mice)

MK gene knockout mice were produced by well known methods (Japanese published unexamined patent application number 2002-85058; Nakamura, E. et al., Genes Cells 3: 811-822).

(Antigen Preparation)

Human MK mRNA was prepared from Wilms' tumor-derived cultivated cell strain G-401 (Tsutsui, J. et al., Biochem. Biophys. Res. Commun. 176: 792-797, 1991). Human MK cDNA having EcoRI-recognizing sites at both ends of the MK-coding region was prepared by 30 cycles (each cycle comprising a temperature change of 93 deg. C. to 37 deg. C. to 72 deg. C.) of PCR (Polymerase Chain Reaction) of using a sense PCR primer: 5'-GCGGAATTCATGCAGCAC-CGAGGCTTCCTC-3' (SEQ ID NO.: 4) and antisense PCR primer: 5'-GCGGAATTCCTAGTCCTTTCCCTTCCCTTT-3' (SEQ ID No.: 5), which were designed such that it contains the sequence recognized by restriction enzyme EcoRI (5'-GAATTC-3'), and using human MK mRNA as the template.

A recombinant expression vector was prepared by EcoRI digesting MK cDNA and the expression vector pHIL301 (containing histidine- and neomycin-resistance gene; see Japanese published unexamined patent application number H02-104292 and European patent application laid-open number 0339568) for yeast (*Pichia pastoris* GS115, hereinafter referred to as "*Pichia* yeast GS115"), and coupling them using a ligation kit (Takara Shuzo Co., Ltd.).

The recombinant expression vector prepared as described above was introduced into *Pichia* yeast GS115 (Invitrogen Corporation) using the electroporation method. A plurality of clones having the target MK gene was obtained by culturing *Pichia* yeast GS115 into which the vector had been introduced in a medium not containing histidine but containing G418. The obtained clones were cultured while induced by methanol. The culture supernatant was collected, and secretion of MK was verified by Western blotting analysis using rabbit anti-murine MK polyclonal antibodies.

One of the clones that secreted MK into the culture supernatant by induction was named T3L-50-4P, and this clone was cultured (see Japanese published unexamined patent application number H07-39889). The MK secretion product was collected from the culture supernatant, and purified by ion-exchange chromatography and affinity chromatography using a heparin column, and then high-purity MK was obtained.

(Immunity)

The MK knockout mice were immunized with MK, an antigen. The antigen formulation was prepared by dissolving 10 g per mouse of the antigen in 0.1 mL of physiological saline to form an antigen solution and mixing the antigen solution with 0.1 mL of FCA to be emulsified, and then administered subcutaneously in the dorsal skin of the mice. The mice were immunized eight times at two-week intervals.

For the eighth immunization, the mice were injected 0.1 mL of the antigen solution containing 10 g of the antigen to the caudal vein.

The blood antibody level was assayed by ELISA using the serum collected from the ocular fundus of the mice on the sixth day after the fourth immunization and on the eighth day after the sixth immunization.

The ELISA method was implemented as follows. First, the antigen solution was prepared to a concentration of 1.0 g/mL with PBS (pH=7.2 to 7.4), and dispensed into a 96-well assay plate (manufactured by Falcon Corp., 353912) at a rate of 50 L/well, and then the plate was incubated overnight at 4 deg. C. to immobilize the antigen. The immobilized antigen was washed three times with 0.05% Tween-PBS. Then 100 L of four fold dilution of Block Ace (produced by Dainippon Pharmaceutical Co.) was added into each well, and then the plate was incubated for two hours at 37 deg. C. to block. The blocked wells were washed three times with 0.05% Tween-PBS, and then 50 L of the culture supernatant was added to each well the plate containing the culture supernatant was incubated for one hour at 37 deg. C., and then washed three times with 0.05% Tween-PBS. 50 L/well of ten-fold Block Ace dilution of goat anti-murine IgG+IgM HRP conjugate (produced by BioSouce Corp., AMI3704) diluted 10000-fold was added as secondary antibodies, and then let the plate was incubated for one hour at 37 deg. C. After washing three times with 0.05% Tween-PBS, 50 L of HRP substrate (25 mL of substrate solution (10.206 mg/mL of citric acid hydrate and 36.82 mg/mL of disodium hydrogen phosphate in distilled water), 10 mg of OPD and 5 L of 30% H2O2) was added into each well, and the plate was incubated in the dark at room temperature for 20 minutes. The reaction was stopped by adding 50 L/well of 1 N sulfuric acid, and the absorbance was measured at a wavelength of 492 nm. The antibody levels were sufficiently high in the ELISA performed on the eighth day after the sixth immunization, so the cells were fused three days after two additional immunizations.

(Cell Fusion)

The mice were held and their chest region was wiped with alcohol-soaked cotton, then blood was collected from their heart using a 2.5 mL syringe and 23 G needle. After the blood was collected, the mice were placed in a beaker containing 20 mL of alcohol for disinfection for approximately three minutes. The collected blood was placed in a 1.5 mL tube and incubated for one hour at 37 deg. C., followed by overnight at 4 deg. C., and then centrifuged for 10 minutes at 3000 rpm. The serum was transferred to another 1.5 mL tube; added 0.05% sodium azide, and stored at 4 deg. C.

The epithelium of the mice from which the blood had been collected was peeled using scissors and tweezers. Then, the endothelium was lifted, a slit was made, and the spleen was excised. Five petri dishes had been prepared in advance by dispensing 200 mL of RPMI 1640 SP culture medium in each. The excised spleen was washed five times, once in each of the five petri dishes, successively. After washing, the spleen was placed on a mesh strainer and several cuts were made in the spleen with scissors. The spleen was then strained through the mesh strainer with a glass rod. The strainer was washed with RPMI 1640 SP culture medium, and the splenocytes were collected in 40 mL glass centrifuge tubes. The collected splenocytes were centrifuged for 10 minutes at 1200 rpm, and the supernatant was drawn up into a suction pipette. 40 mL of RPMI 1640 SP culture medium was added into the tube, and the tube was centrifuged for 10 minutes at 1200 rpm. The obtained splenocytes were placed in additional 40 mL of RPMI 1640 SP culture medium and agitated thoroughly. The number of cells was counted using a blood cell counter.

Myeloma cells (P3U1) in the petri dish were collected in a 50 mL centrifuge tube by blowing them in using a pipette. The cells were centrifuged for five minutes at 1000 rpm, the supernatant was removed by a suction pipette, and then 40 mL of RPMI 1640 SP culture medium was added into the tube. The tube was centrifuged for five minutes at 1000 rpm, and 40 mL of RPMI 1640 SP culture medium was added to the obtained myeloma cells and agitated thoroughly. The number of cells was counted using a blood cell counter.

Based on the results of the number of cells obtained as set forth above, the myeloma cells were placed in the 50 mL glass centrifuge tube in which the splenocytes had been stored such that the ratio of the number of splenocytes to the number of myeloma cells would be 5:1. After mixing the cells, they were centrifuged for 10 minutes at 1200 rpm, and the supernatant was drawn up into a suction pipette, which was then tapped. After tapping, 1 mL of PEG (polyethylene glycol) was slowly added over one minute while mixing, and the solution was continued to be mixed for an additional two minutes. After mixing with the PEG, 1 mL of RPMI 1640 SP culture medium, which had been preheated to 37 deg. C. in a water bath, was slowly added over one minute while mixing. This process was repeated three times. Then, 10 mL of RPMI 1640 SP culture medium, which had been preheated to 37 deg. C., was slowly added over three minutes while mixing. After adding the culture medium, the culture fluid was heated for five minutes in a 5% CO2 incubator at 37 deg. C., and then centrifuged for five minutes at 1000 rpm. The supernatant was drawn up into a suction pipette, which was then tapped.

After tapping, (number of plates on which the cells are to be seeded)×10 mL of RPMI 1640 SP, 15% FCS, HAT culture medium was blown onto the cells, and using a series of eight micropipettes (each 100 L) and exclusive trays, a 96-well plate was seeded with the cells using a yellow tip. The cells were cultured for 7 to 14 days in a 5% CO2 incubator at 37 deg. C., and then the antibody production capacity was screened by ELISA according to the colony growth.

(Selection of Anti-MK-Positive Antibody-Producing Hybridomas)

Ten days after cell fusion, 12 wells among the 96-well culture plate whose supernatant absorbance found to be significantly higher by ELISA were selected for cloning samples. The number of hybridomas was counted, and the hybridomas were seeded on a 96-well culture plate so that three rows had 5 cells/well, three rows had 1 cell/well, and two rows had 0.5 cells/well. Furthermore, 1×10<6> cells of feeder cells were seeded on each well. Colonies were counted five days after cloning, and wells having single colonies were verified. The culture medium was replaced every two to three days, and when a colony grown to cover one-third of a well, wells indicating a positive reaction by a single colony were selected by ELISA, and the cells which was obtained from the wells wherein a single colony was found to have a positive reaction by ELISA, and which was in a good condition, was established as IP-13.

Next, the anti-MK antibody (IP-13) obtained by the method set forth above was examined for possible inhibitory activity to the MK which inhibit the increase in number of CD4-positive, CD25-positive T cells, using the same method employed in example 4. CD4-positive T cells were isolated from wild-type murine spleens, and cultured in the presence of IP-13 (30 g/mL), MOG35-55 (30 g/mL) and APC. After five days cultivation, the proportion of CD4-positive, CD25-positive T cells among the CD4-positive T cells was assayed using a flow cytometer. An experiment in which IgG was used instead of IP-13 antibodies was conducted concurrently as a control.

Figure 7:
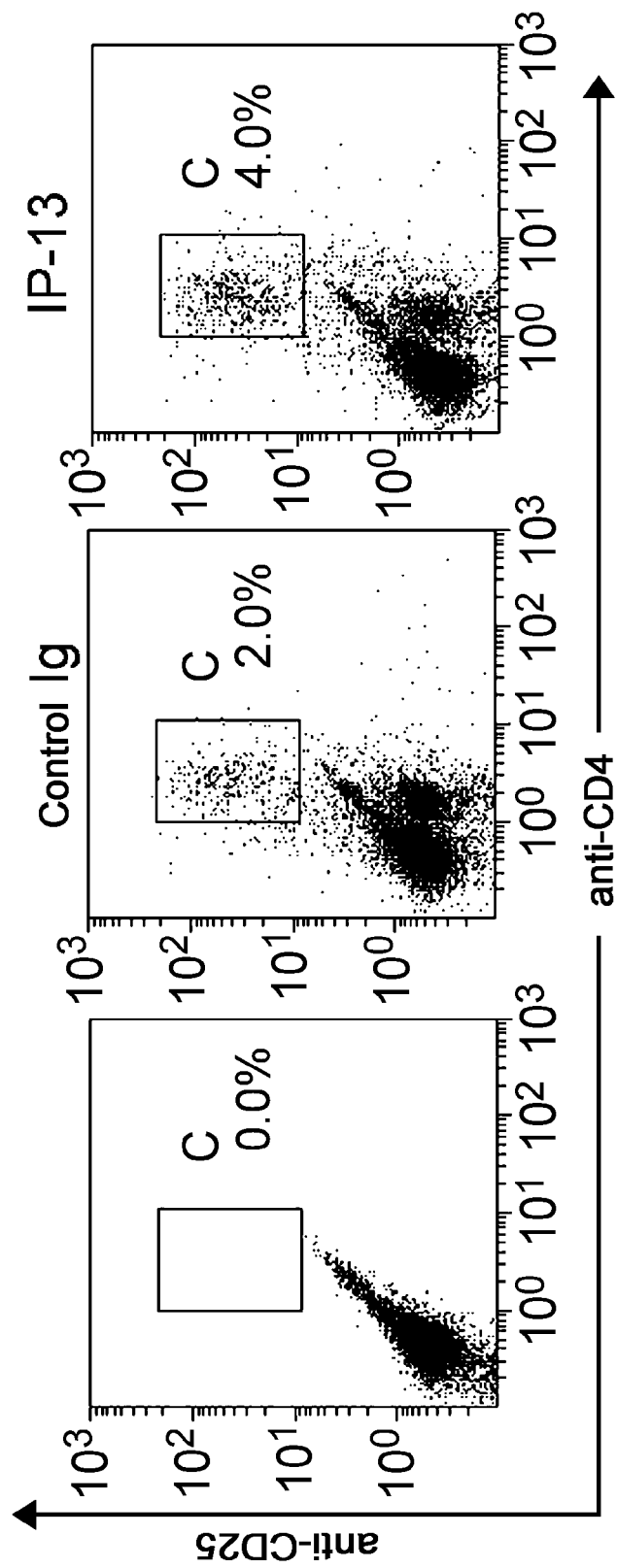
FIG. 7 The figure indicates the results of analyzing the effect of the addition of anti-MK antibodies to the dynamics of CD4-positive, CD25-positive T cells in EAE model mice. The proportion of CD4-positive, CD25-positive T cells was detected after stimulating CD4-positive T cells derived from the spleens of EAE-induced mice with 30 g/mL of MOG35-55 and APC for five days in the presence of anti-MK antibodies (IP-13) or control antibodies (IgG).

The results revealed that while the proportion of CD4-positive, CD25-positive T cells was 2% in the control experiment, the proportion of CD4-positive, CD25-positive T cells had increased to 4% in the experiment in which IP-13 had been added. These results indicated that the activity of MK to inhibit the increase in number of CD4-positive, CD25-positive cells can be inhibited by using anti-MK antibodies (FIG. 7).

Example 8

Observation of Changes in Clinical Symptoms in EAE Model Mice Resulting from the Addition of Anti-MK Antibodies Anti-MK antibodies were administered to wild-type mice exhibiting clinical symptoms in which experimental autoimmune encephalomyelitis (EAE) had been induced by the method set forth in example 1, and their clinical symptoms were observed.

First, MOG35-55 was administered to wild-type EAE model mice (C57BL-6, female, eight weeks old), and then anti-MK antibody (IP14) was administered to the mice on days 0, 3, 7, 10, 14, 17, 21 and 24 (a total of eight dosage) after the administration of MOG35-55. The mice were divided into four groups (five mice per group), and the each group was treated with 75 mg/kg body weight, 7.5 mg/kg body weight, 0.75 mg/kg body weight or 0 mg/kg body weight (control) of anti-MK antibodies through the caudal vein. Clinical scores (0: no symptoms; 1: loss of tail tone; 2: laying face up, unable to rise; 3: unstable gait; 4: slight hind limb paralysis; 5: severe hind limb paralysis; 6: death, were assigned daily to evaluate the clinical symptoms.

Figure 8:
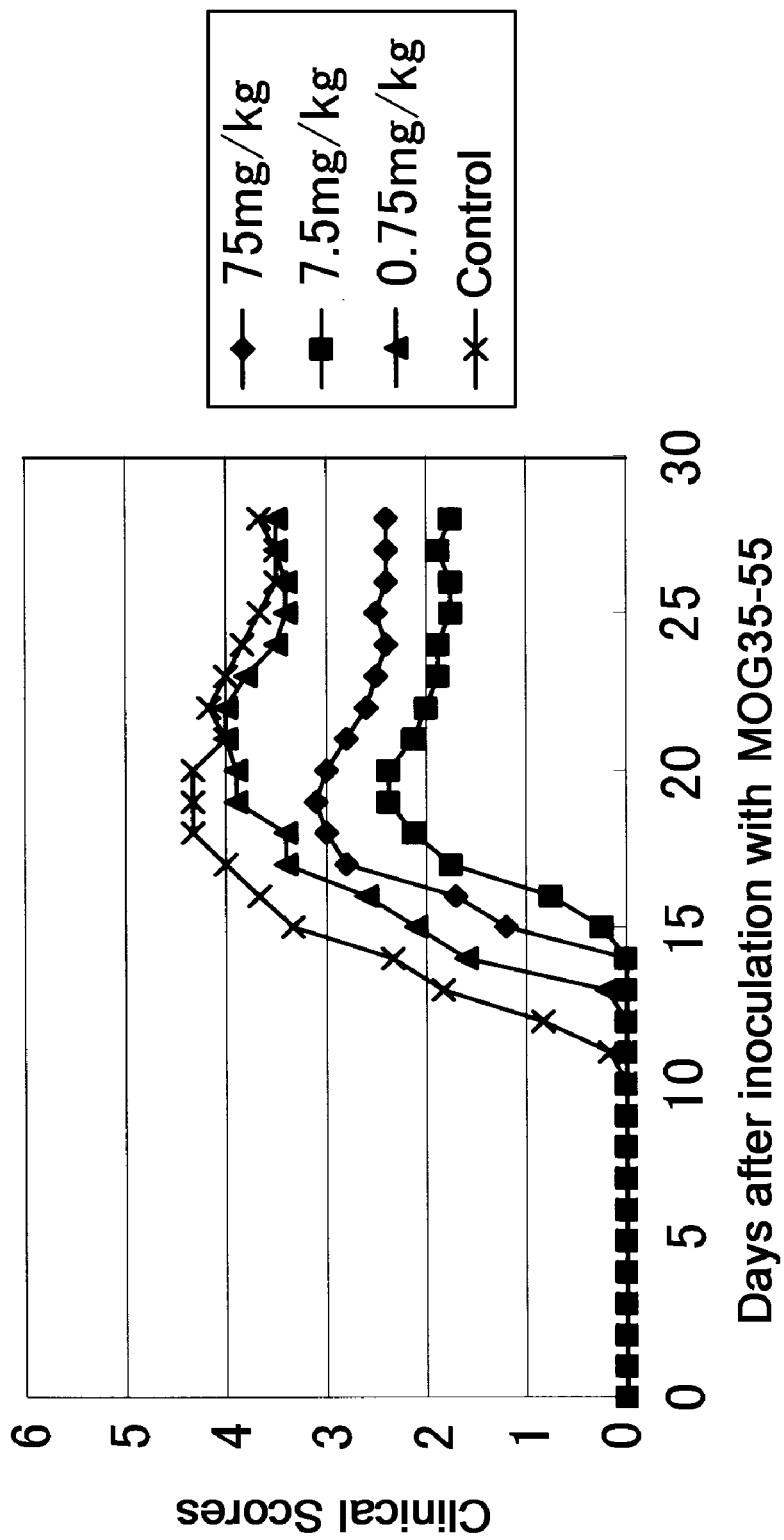
FIG. 8 The figure indicates the observed results of changes in clinical symptoms in EAE model mice resulting from the administration of anti-MK antibodies. Wild-type EAE model mice (C57BL-6, eight weeks old) were administered anti-MK antibodies (IP14), on days 0, 3, 7, 10, 14, 17, 21 and 24 (a total of eight times) following administration of MOG35-55. The mice were divided into four groups (five mice per group), and were administered anti-MK antibodies in the caudal vein at the following doses per mouse weight (kg): group 1 (black diamond): 75 mg/kg; group 2 (black square) 7.5 mg/kg; group 3 (black triangle) 0.75 mg/kg; and group 4 (X, control) 0 mg/kg. The y-axis represents the mean values of clinical scores (0: no symptoms; 1: loss of tail tone; 2: laying face up, unable to rise; 3: unstable gait; 4: slight hind limb paralysis; 5: severe hind limb paralysis; 6: death).

The results indicated mitigation of clinical symptoms in the groups of mice with administration of anti-MK antibodies (FIG. 8). Specifically, the groups of mice with administration of anti-MK antibodies after being inoculated with MOG35-55 exhibited delayed disease onset and mitigation of severity of disease.

Example 9

Experiment of Disease Onset Inhibition in EAE Model Mice Using MK Aptamers

MK aptamers were administered to wild-type mice in which experimental autoimmune encephalomyelitis (EAE) had been induced by the method set forth in example 1, and the inhibitory effect on EAE onset in the mice was observed.

Aptamers that specifically bind to MK were produced using the SELEX method. One of the obtained aptamers was shortened to a length that could be chemically synthesized. In addition, aptamer A, in which nuclease resistance had been enhanced through chemical modification was obtained.

Inhibitory activity of aptamer A to human MK cell migration activity was examined using UMR106 cells (ATCC No. CRL1661), which are rat osteoblast precursor cells. The external surface of chemotaxicell membrane (membrane pore size 8 m, produced by Kurabo Industries Ltd.) was coated with 30 L of 1.5 M MK to immobilize the MK on the external surface of the membrane. The chemotaxicells on which MK had been immobilized were placed on a 24-well culture plate containing 500 L of culture medium (0.3% bovine serum albumin added, Dulbecco's Modified Eagle's Medium) containing 500 nM aptamer. 200 L of UMR106 cells were placed in the internal lamina of the chemotaxicell chamber at a concentration of $1\times10^{6}$ cells/mL, and cultured for four hours at 37 deg. C. The residual cells in the internal lamina of the chemotaxicell chamber were removed, and the cells that had penetrated into and adhered to the MK-coated surface were fixed with methanol. The chemotaxicell chamber was immersed in a 1% aqueous crystal violet solution for 30 minutes to stain the cells. The chemotaxicell chamber was washed with distilled water and dried, and then the pigment was extracted with 200 L of a mixture of 1% SDS and 1% tritonX100. 150 L of the extract was transferred to a 96-well microplate, and the absorbance at 590 nm was measured. The results revealed that aptamer A has strong cell migration-inhibiting activity. If the number of cells that had migrated when no aptamer had been added was set at 100, the number of cells that had migrated when aptamer A had been added was approximately 2.3, hence, a 98% inhibitory activity was verified. Meanwhile, the RNA used as the control indicated no inhibitory activity.

Figure 9:
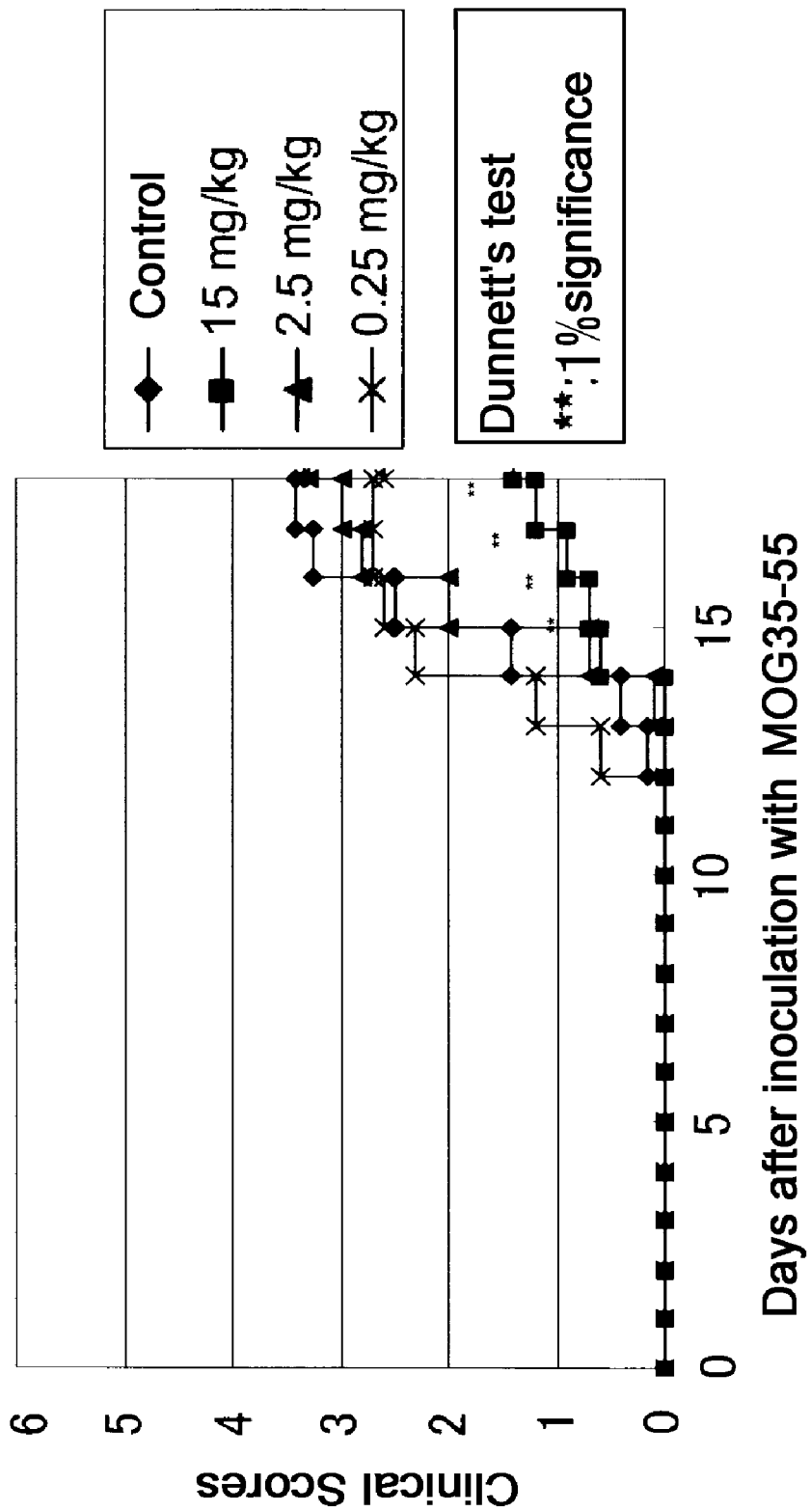
FIG. 9 The figure indicates the observed results of changes in clinical symptoms in EAE model mice resulting from the administration of MK aptamers. Wild-type EAE model mice (C57BL-6, eight weeks old) were administered intraperitoneally with aptamers for a total of ten doses every other day following administration of MOG35-55. The doses of the aptamers were as follows: group 1 (black square): 15 mg/kg; group 2 (black triangle): 2.5 mg/kg; group 3 (X): 0.25 mg/kg; and group 4 (diamond, control): 0 mg/kg. The y-axis represents the mean values of clinical scores (0: no symptoms; 1: loss of tail tone; 2: laying face up, unable to rise; 3: unstable gait; 4: slight hind limb paralysis; 5: severe hind limb paralysis; 6: death). **: $p<0.01$.

It was examined whether aptamer A plays a role in the increase in number of CD4-positive, CD25-positive regulatory T cells. The experiment was conducted in the same manner as described in example 7. CD4-positive T cells were isolated from the spleens of C57BL-6 mice exhibiting clinical symptoms of EAE in the fourth week after treating with MOG, and said cells ($2\times10^{5}$ cells/well) were cultured in vitro in the presence of MOG35-55 (20 g/mL) and APC for three days after addition of aptamer A. CD4-positive, CD25-positive cell expression was analyzed by FACS. Furthermore, intracellular FOXP3 was detected by flow cytometry, by simultaneously staining CD4-positive cells using the anti-mouse FOXP3 staining set (manufactured by e-Bioscience Corp.). The results of the experiment indicated that the presence proportion of CD4-positive, CD25-positive regulatory T cells was 6.2% in the system in which PBS had been added as the control, while the presence proportion of CD4-positive, CD-25-positive regulatory T cells was 11% in the system in which 125 nM of aptamer A had been added, indicating that the addition of aptamers increases the presence of CD4-positive, CD25-positive regulatory T cells. FOXP3 expression, which is related to the production and differentiation of regulatory T cells, was also investigated. While expression was verified in 25% of the CD4-positive cells in the system in which PBS had been added as the control, expression was increased and verified in 33% of the CD4-positive cells in the system in which 125 nM of aptamer A had been added. These results indicated that the number of CD4-positive, CD25-positive regulatory T cells increases by the addition of aptamer A. An experiment on inhibition of disease onset in EAE model mice using aptamer A was conducted. Aptamer A was administered intraperitoneally at the dosage of 15 mg/kg of body weight, 2.5 mg/kg of body weight, 0.25 mg/kg or 0 mg/kg of body weight (control), for a total of 10 doses every other day from the day of MOG treatment, to EAE model mice, which were eight-week-old mice (C57BL-6, female) treated with MOG. Each group consists of five to six mice. The mice were observed daily, and each mouse was scored for clinical symptoms based on clinical scores (0: no symptoms; 1: loss of tail tone; 2: laying face up, unable to rise; 3: unstable gait; 4: slight hind limb paralysis; 5: severe hind limb paralysis; 6: death). The results indicated that p 0.01 for the 15 mg/kg group compared to the control group on days 15, 16, 17 and 18 after treatment with MOG, which showed a significant difference statistically (FIG. 9). Dunnett's test was used for statistical analysis. The effect of delaying disease onset was observed in the 15 mg/kg and 2.5 mg/kg groups. These findings indicated that aptamers that specifically bind to MK, which are MK-inhibitors, can be utilized as a therapeutic drug for multiple sclerosis, which is a disease associated with the reduction of CD4-positive, CD25-positive regulatory T cells.

INDUSTRIAL APPLICABILITY

Inhibiting MK expression or activity increases the number of regulatory T cells, hence, the present invention can be utilized as for treating or preventing diseases associated with the functional disorder of regulatory T cells, such as multiple sclerosis, by inhibiting MK through administration of an MK aptamer. In addition, MK aptamers can be used as a therapeutic, preventive or diagnostic agent for diseases associated with the functional disorder of regulatory T cells. The diagnostic method of the present invention can be used as a method for diagnosing diseases associated with the functional disorder of regulatory T cells.

The invention claimed is:

1. A method for increasing the number of CD4-positive, CD25-positive regulatory T cells in a subject with a decreased number of the CD4-positive, CD25-positive regulatory T cells due to inhibition of proliferation of the CD4-positive, CD25-positive regulatory T cells by Midkine (MK), comprising administering to the subject an effective amount of a MK inhibitor, wherein:
the MK inhibitor is an aptamer against Midkine,
the MK comprises the amino acid sequence of SEQ ID NO: 2,
the number of the CD4-positive, CD25-positive regulatory T cells in the subject is increased, and
the subject has multiple sclerosis.

2. A method for the treatment of multiple sclerosis comprising administering a Midkine (MK) inhibitor to a subject having multiple sclerosis, wherein the MK inhibitor is an aptamer against Midkine and wherein the MK comprises the amino acid sequence of SEQ ID NO: 2.

* * * * *

SEQUENCE LISTING

```
<160> NUMBER OF SEQ ID NOS: 5

<210> SEQ ID NO 1
<211> LENGTH: 562
<212> TYPE: DNA
<213> ORGANISM: Homo sapiens
<220> FEATURE:
<221> NAME/KEY: CDS
<222> LOCATION: (1)..(432)

<400> SEQUENCE: 1 atg cag cac cga ggc ttc ctc ctc ctc acc ctc ctc gcc ctg ctg gcg      48
Met Gln His Arg Gly Phe Leu Leu Leu Thr Leu Leu Ala Leu Leu Ala
1               5                  10                  15 ctc acc tcc gcg gtc gcc aaa aag aaa gat aag gtg aag aag ggc ggc      96
Leu Thr Ser Ala Val Ala Lys Lys Lys Asp Lys Val Lys Lys Gly Gly
                20                  25                  30 ccg ggg agc gag tgc gct gag tgg gcc tgg ggg ccc tgc acc ccc agc     144
Pro Gly Ser Glu Cys Ala Glu Trp Ala Trp Gly Pro Cys Thr Pro Ser
            35                  40                  45 agc aag gat tgc ggc gtg ggt ttc cgc gag ggc acc tgc ggg gcc cag     192
Ser Lys Asp Cys Gly Val Gly Phe Arg Glu Gly Thr Cys Gly Ala Gln
        50                  55                  60 acc cag cgc atc cgg tgc agg gtg ccc tgc aac tgg aag aag gag ttt     240
Thr Gln Arg Ile Arg Cys Arg Val Pro Cys Asn Trp Lys Lys Glu Phe
65                  70                  75                  80 gga gcc gac tgc aag tac aag ttt gag aac tgg ggt gcg tgt gat ggg     288
Gly Ala Asp Cys Lys Tyr Lys Phe Glu Asn Trp Gly Ala Cys Asp Gly
                85                  90                  95 ggc aca ggc acc aaa gtc cgc caa ggc acc ctg aag aag gcg cgc tac     336
Gly Thr Gly Thr Lys Val Arg Gln Gly Thr Leu Lys Lys Ala Arg Tyr
                100                 105                 110 aat gct cag tgc cag gag acc atc cgc gtc acc aag ccc tgc acc ccc     384
Asn Ala Gln Cys Gln Glu Thr Ile Arg Val Thr Lys Pro Cys Thr Pro
            115                 120                 125 aag acc aaa gca aag gcc aaa gcc aag aaa ggg aag gga aag gac tag     432
Lys Thr Lys Ala Lys Ala Lys Ala Lys Lys Gly Lys Gly Lys Asp
        130                 135                 140 acgccaagcc tggatgccaa ggagcccctg gtgtcacatg gggcctggcc cacgccctcc    492
ctctcccagg cccgagatgt gacccaccag tgccttctgt ctgctcgtta gctttaatca    552
atcatgcccc                                                           562

<210> SEQ ID NO 2
<211> LENGTH: 143
<212> TYPE: PRT
<213> ORGANISM: Homo sapiens

<400> SEQUENCE: 2

Met Gln His Arg Gly Phe Leu Leu Leu Thr Leu Leu Ala Leu Leu Ala
1               5                  10                  15

Leu Thr Ser Ala Val Ala Lys Lys Lys Asp Lys Val Lys Lys Gly Gly
```

```
                    20                  25                  30

Pro Gly Ser Glu Cys Ala Glu Trp Ala Trp Gly Pro Cys Thr Pro Ser
            35                  40                  45

Ser Lys Asp Cys Gly Val Gly Phe Arg Glu Gly Thr Cys Gly Ala Gln
        50                  55                  60

Thr Gln Arg Ile Arg Cys Arg Val Pro Cys Asn Trp Lys Lys Glu Phe
65                  70                  75                  80

Gly Ala Asp Cys Lys Tyr Lys Phe Glu Asn Trp Gly Ala Cys Asp Gly
                85                  90                  95

Gly Thr Gly Thr Lys Val Arg Gln Gly Thr Leu Lys Lys Ala Arg Tyr
            100                 105                 110

Asn Ala Gln Cys Gln Glu Thr Ile Arg Val Thr Lys Pro Cys Thr Pro
            115                 120                 125

Lys Thr Lys Ala Lys Ala Lys Ala Lys Lys Gly Lys Gly Lys Asp
        130                 135                 140

<210> SEQ ID NO 3
<211> LENGTH: 21
<212> TYPE: PRT
<213> ORGANISM: Artificial sequence
<220> FEATURE:
<223> OTHER INFORMATION: Synthetic construct; myelin oligodendrocyte
      glycoprotein peptide 35-55

<400> SEQUENCE: 3

Met Glu Val Gly Trp Tyr Arg Ser Pro Phe Ser Arg Val Val His Leu
1               5                   10                  15

Tyr Arg Asn Gly Lys
            20

<210> SEQ ID NO 4
<211> LENGTH: 30
<212> TYPE: DNA
<213> ORGANISM: Artificial sequence
<220> FEATURE:
<223> OTHER INFORMATION: Synthetic construct; primer sequence

<400> SEQUENCE: 4
gcggaattca tgcagcaccg aggcttcctc                                    30

<210> SEQ ID NO 5
<211> LENGTH: 30
<212> TYPE: DNA
<213> ORGANISM: Artificial sequence
<220> FEATURE:
<223> OTHER INFORMATION: Synthetic construct; primer sequence

<400> SEQUENCE: 5
gcggaattcc tagtcctttc ccttcccttt                                    30
```